US011548921B2

(12) United States Patent
Love et al.

(10) Patent No.: US 11,548,921 B2
(45) Date of Patent: Jan. 10, 2023

(54) NANONETS AND SPHERICAL PARTICLES

(71) Applicant: THE JAMES HUTTON INSTITUTE, Dundee Tayside (GB)

(72) Inventors: Andrew John Love, Dundee Tayside (GB); Mikhail Emmanuilovich Talianski, Dundee Tayside (GB); Kara McGeachy, Dundee Tayside (GB)

(73) Assignee: The James Hutton Institute, Dundee Tayside (GB)

( * ) Notice: Subject to any disclaimer, the term of this patent is extended or adjusted under 35 U.S.C. 154(b) by 26 days.

(21) Appl. No.: 16/617,944

(22) PCT Filed: May 31, 2018

(86) PCT No.: PCT/GB2018/051495
§ 371 (c)(1),
(2) Date: Nov. 27, 2019

(87) PCT Pub. No.: WO2018/220386
PCT Pub. Date: Dec. 6, 2018

(65) Prior Publication Data
US 2020/0190148 A1 Jun. 18, 2020

(30) Foreign Application Priority Data

May 31, 2017 (GB) ..................................... 1708675

(51) Int. Cl.
*C07K 14/315* (2006.01)
*C07K 14/005* (2006.01)

(52) U.S. Cl.
CPC .......... *C07K 14/315* (2013.01); *C07K 14/005* (2013.01); *C07K 2319/02* (2013.01); *C07K 2319/20* (2013.01); *C07K 2319/735* (2013.01)

(58) Field of Classification Search
None
See application file for complete search history.

(56) References Cited

FOREIGN PATENT DOCUMENTS

WO WO 2016/112921 A1 7/2016
WO WO 2017/070742 A1 5/2017

OTHER PUBLICATIONS

Smith et al. Modified Tobacco mosaic virus particles as scaffolds for display of protein antigens for vaccine applications. Virology 348 (2006) 475-488. (Year: 2006).*
Ekaterina et al (2014) Complexes assembled from TMV-derived spherical particles and entire virions of heterogeneous nature, Journal of Biomolecular Structure and Dynamics, 32:8, 1193-1201, DOI: 10.1080/07391102.2013. (Year: 2014) Abstract Only.*

(Continued)

*Primary Examiner* — Michelle S Horning
(74) *Attorney, Agent, or Firm* — Alston & Bird LLP

(57) ABSTRACT

The present invention relates to macromolecular complexes comprising micron-scale networks which include binding motifs thereon which allow the covalent bonding of the micron-scale networks to particles which provide nanoscale display surfaces. In particular the present invention relates to micron-scale networks of TMV coat proteins comprising a peptide tag (e.g. SpyTag) and particles providing a nanoscale display surface comprising GFP and a corresponding binding protein (e.g. SpyCatcher) wherein the peptide tag and binding protein pair are capable of spontaneously forming a covalent bond.

17 Claims, 10 Drawing Sheets

Specification includes a Sequence Listing.

(56) References Cited

OTHER PUBLICATIONS

Figure 1:
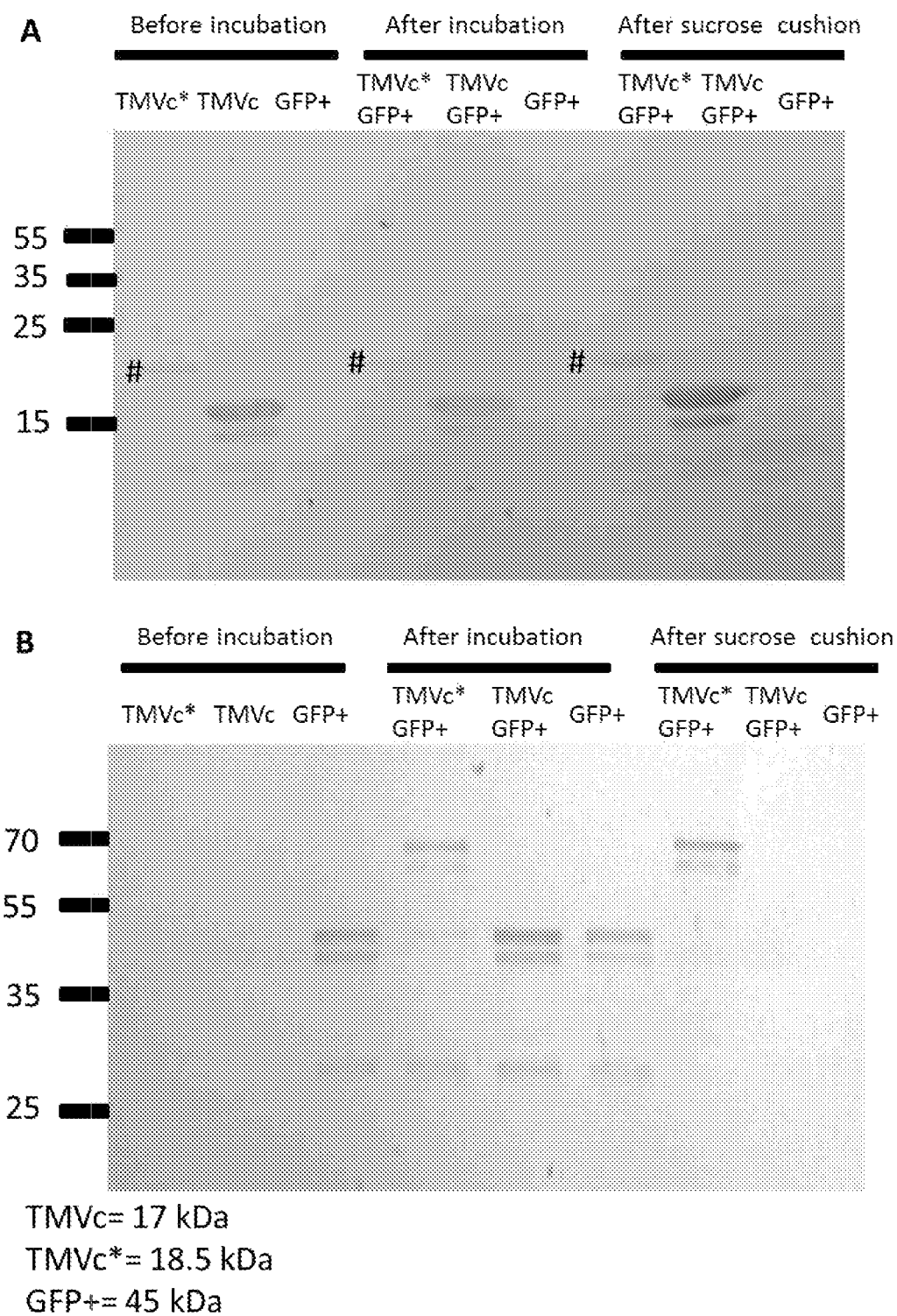

Brown et al., "Carboxylate-Directed In Vivo Assembly of Virus-like Nanorods and Tubes for the Display of Functional Peptides and Residues," Biomacromolecules, 14(9): 3123-3129, (2013).
Brune et al., "Plug-and-Display: decoration of Virus-Like Particles via isopeptide bonds for modular immunization," Scientific Reports, 6:19234, (2016).
Röder et al., "Engineering Potato Virus X Particles for a Covalent Protein Based Attachment of Enzymes," 13(48): 1702151, (2017).
WIPO Application No. PCT/GB2018/051495, PCT International Search Report and Written Opinion of the International Searching Authority dated Sep. 28, 2018.

\* cited by examiner

TMVc= 17 kDa
TMVc*= 18.5 kDa
GFP+= 45 kDa (SEQ ID NO: 11)
TMV CP-GGGGS-SpyCatcher His (SEQ ID NO: 12)
TMV CP-GGGGS-SpyTag His

SEQUENCE LISTING

<160> NUMBER OF SEQ ID NOS: 13

<210> SEQ ID NO 1
<211> LENGTH: 139
<212> TYPE: PRT
<213> ORGANISM: Artificial Sequence
<220> FEATURE:
<223> OTHER INFORMATION: SpyCatcher Sequence

<400> SEQUENCE: 1

Met Ser Tyr Tyr His His His His His His Asp Tyr Asp Ile Pro Thr
1               5                   10                  15

Thr Glu Asn Leu Tyr Phe Gln Gly Ala Met Val Asp Thr Leu Ser Gly
            20                  25                  30

Leu Ser Ser Glu Gln Gly Gln Ser Gly Asp Met Thr Ile Glu Glu Asp
        35                  40                  45

Ser Ala Thr His Ile Lys Phe Ser Lys Arg Asp Glu Asp Gly Lys Glu
    50                  55                  60

Leu Ala Gly Ala Thr Met Glu Leu Arg Asp Ser Ser Gly Lys Thr Ile
65                  70                  75                  80

Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Lys Ala Thr Lys Gly Asp Ala His Ile
    130                 135

<210> SEQ ID NO 2
<211> LENGTH: 13
<212> TYPE: PRT
<213> ORGANISM: Artificial Sequence
<220> FEATURE:
<223> OTHER INFORMATION: SpyTag

<400> SEQUENCE: 2

Ala His Ile Val Met Val Asp Ala Tyr Lys Pro Thr Lys
1               5                   10

<210> SEQ ID NO 3
<211> LENGTH: 8
<212> TYPE: PRT
<213> ORGANISM: Artificial Sequence
<220> FEATURE:
<223> OTHER INFORMATION: SpyTag truncated

<400> SEQUENCE: 3

Ala His Ile Val Met Val Asp Ala
1               5

<210> SEQ ID NO 4
<211> LENGTH: 159
<212> TYPE: PRT
<213> ORGANISM: Artificial Sequence
<220> FEATURE:
<223> OTHER INFORMATION: TMV CP (modified for self assembly in bacteria)

<400> SEQUENCE: 4

Met Ser Tyr Ser Ile Thr Thr Pro Ser Gln Phe Val Phe Leu Ser Ser
1               5                   10                  15

```
Ala Trp Ala Asp Pro Ile Glu Leu Ile Asn Leu Cys Thr Asn Ala Leu
            20                  25                  30

Gly Asn Gln Phe Gln Thr Gln Ala Arg Thr Val Val Gln Arg Gln
        35                  40                  45

Phe Ser Gln Val Trp Lys Pro Ser Pro Gln Val Thr Val Arg Phe Pro
 50                  55                  60

Asp Ser Asp Phe Lys Val Tyr Arg Tyr Asn Ala Val Leu Asn Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
                115                 120                 125

Leu Ile Val Glu Leu Ile Arg Gly Thr Gly Ser Tyr Asn Arg Ser Ser
            130                 135                 140

Phe Glu Ser Ser Ser Gly Leu Val Trp Thr Ser Gly Pro Ala Thr
145                 150                 155
```

<210> SEQ ID NO 5
<211> LENGTH: 172
<212> TYPE: PRT
<213> ORGANISM: Artificial Sequence
<220> FEATURE:
<223> OTHER INFORMATION: TMV CP with C-terminal SpyTag

<400> SEQUENCE: 5

```
Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
            20                  25                  30

Gly Asn Gln Phe Gln Thr Gln Ala Arg Thr Val Val Gln Arg Gln
        35                  40                  45

Phe Ser Gln Val Trp Lys Pro Ser Pro Gln Val Thr Val Arg Phe Pro
 50                  55                  60

Asp Ser Asp Phe Lys Val Tyr Arg Tyr Asn Ala Val Leu Asn Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
                115                 120                 125

Leu Ile Val Glu Leu Ile Arg Gly Thr Gly Ser Tyr Asn Arg Ser Ser
            130                 135                 140

Phe Glu Ser Ser Ser Gly Leu Val Trp Thr Ser Gly Pro Ala Thr Ala
145                 150                 155                 160

His Ile Val Met Val Asp Ala Tyr Lys Pro Thr Lys
                165                 170
```

<210> SEQ ID NO 6
<211> LENGTH: 265
<212> TYPE: PRT
<213> ORGANISM: Artificial Sequence
<220> FEATURE:
<223> OTHER INFORMATION: GFP sequence

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65              70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
            245                 250                 255

Ala Gly Pro Gly Ser Thr Gly Ser Arg
        260                 265
```

<210> SEQ ID NO 7
<211> LENGTH: 407
<212> TYPE: PRT
<213> ORGANISM: Artificial Sequence
<220> FEATURE:
<223> OTHER INFORMATION: SpyCatcher-GFP

<400> SEQUENCE: 7

```
Met Ser Tyr Tyr His His His His His His Asp Tyr Asp Ile Pro Thr
1               5                   10                  15

Thr Glu Asn Leu Tyr Phe Gln Gly Ala Met Val Asp Thr Leu Ser Gly
            20                  25                  30

Leu Ser Ser Glu Gln Gly Gln Ser Gly Asp Met Thr Ile Glu Glu Asp
        35                  40                  45

Ser Ala Thr His Ile Lys Phe Ser Lys Arg Asp Glu Asp Gly Lys Glu
    50                  55                  60

Leu Ala Gly Ala Thr Met Glu Leu Arg Asp Ser Ser Gly Lys Thr Ile
65              70                  75                  80
```

```
Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Lys Ala Thr Lys Gly Asp Ala His Ile Ala Thr Cys Met Val
130                 135                 140

Ser Lys Gly Glu Glu Leu Phe Thr Gly Val Val Pro Ile Leu Val Glu
145                 150                 155                 160

Leu Asp Gly Asp Val Asn Gly His Lys Phe Ser Val Ser Gly Glu Gly
                165                 170                 175

Glu Gly Asp Ala Thr Tyr Gly Lys Leu Thr Leu Lys Phe Ile Cys Thr
            180                 185                 190

Thr Gly Lys Leu Pro Val Pro Trp Pro Thr Leu Val Thr Thr Leu Thr
        195                 200                 205

Tyr Gly Val Gln Cys Phe Ser Arg Tyr Pro Asp His Met Lys Gln His
    210                 215                 220

Asp Phe Phe Lys Ser Ala Met Pro Glu Gly Tyr Val Gln Glu Arg Thr
225                 230                 235                 240

Ile Phe Phe Lys Asp Asp Gly Asn Tyr Lys Thr Arg Ala Glu Val Lys
                245                 250                 255

Phe Glu Gly Asp Thr Leu Val Asn Arg Ile Glu Leu Lys Gly Ile Asp
            260                 265                 270

Phe Lys Glu Asp Gly Asn Ile Leu Gly His Lys Leu Glu Tyr Asn Tyr
        275                 280                 285

Asn Ser His Asn Val Tyr Ile Met Ala Asp Lys Gln Lys Asn Gly Ile
290                 295                 300

Lys Val Asn Phe Lys Ile Arg His Asn Ile Glu Asp Gly Ser Val Gln
                310                 315                 320
305

Leu Ala Asp His Tyr Gln Gln Asn Thr Pro Ile Gly Asp Gly Pro Val
            325                 330                 335

Leu Leu Pro Asp Asn His Tyr Leu Ser Thr Gln Ser Ala Leu Ser Lys
        340                 345                 350

Asp Pro Asn Glu Lys Arg Asp His Met Val Leu Leu Glu Phe Val Thr
    355                 360                 365

Ala Ala Gly Ile Thr Leu Gly Met Asp Glu Leu Tyr Lys Ser Gly Leu
370                 375                 380

Arg Ser Arg Ala Gln Ala Ser Asn Ser Ala Val Asp Gly Thr Ala Gly
385                 390                 395                 400

Pro Gly Ser Thr Gly Ser Arg
            405

<210> SEQ ID NO 8
<211> LENGTH: 340
<212> TYPE: PRT
<213> ORGANISM: Streptococcus pyogenes

<400> SEQUENCE: 8

Met Lys Leu Arg His Leu Leu Leu Thr Gly Ala Ala Leu Thr Ser Phe
1               5                   10                  15

Ala Ala Thr Thr Val His Gly Glu Thr Val Val Asn Gly Ala Lys Leu
            20                  25                  30
```

Thr Val Thr Lys Asn Leu Asp Leu Val Asn Ser Asn Ala Leu Ile Pro
            35                  40                  45

Asn Thr Asp Phe Thr Phe Lys Ile Glu Pro Asp Thr Thr Val Asn Glu
 50                  55                  60

Asp Gly Asn Lys Phe Lys Gly Val Ala Leu Asn Thr Pro Met Thr Lys
 65                  70                  75                  80

Val Thr Tyr Thr Asn Ser Asp Lys Gly Gly Ser Asn Thr Lys Thr Ala
                 85                  90                  95

Glu Phe Asp Phe Ser Glu Val Thr Phe Glu Lys Pro Gly Val Tyr Tyr
                100                 105                 110

Tyr Lys Val Thr Glu Glu Lys Ile Asp Lys Val Pro Gly Val Ser Tyr
            115                 120                 125

Asp Thr Thr Ser Tyr Thr Val Gln Val His Val Leu Trp Asn Glu Glu
130                 135                 140

Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175

Val Lys Lys Val Ser Gly Thr Gly Gly Asp Arg Ser Lys Asp Phe
                180                 185                 190

Asn Phe Gly Leu Thr Leu Lys Ala Asn Gln Tyr Tyr Lys Ala Ser Glu
                195                 200                 205

Lys Val Met Ile Glu Lys Thr Thr Lys Gly Gly Gln Ala Pro Val Gln
            210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
                260                 265                 270

Ser Pro Gln Asp Gly Ala Val Lys Asn Ile Ala Gly Asn Ser Thr Glu
            275                 280                 285

Gln Glu Thr Ser Thr Asp Lys Asp Met Thr Ile Thr Phe Thr Asn Lys
            290                 295                 300

Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
            340

<210> SEQ ID NO 9
<211> LENGTH: 674
<212> TYPE: PRT
<213> ORGANISM: Enterococcus faecalis

<400> SEQUENCE: 9

Met Thr Lys Ser Val Lys Phe Leu Val Leu Leu Val Met Ile Leu
1                5                  10                  15

Pro Ile Ala Gly Ala Leu Leu Ile Gly Pro Ile Ser Phe Gly Ala Glu
             20                  25                  30

Leu Ser Lys Ser Ser Ile Val Asp Lys Val Glu Leu Asp His Thr Thr
            35                  40                  45

-continued

Leu Tyr Gln Gly Glu Met Thr Ser Ile Lys Val Ser Phe Ser Asp Lys
    50                  55                  60

Glu Asn Gln Lys Ile Lys Pro Gly Asp Thr Ile Thr Leu Thr Leu Pro
65                  70                  75                  80

Asp Ala Leu Val Gly Met Thr Glu Asn Asp Ser Ser Pro Arg Lys Ile
                    85                  90                  95

Asn Leu Asn Gly Leu Gly Glu Val Phe Ile Tyr Lys Asp His Val Val
                100                 105                 110

Ala Thr Phe Asn Glu Lys Val Glu Ser Leu His Asn Val Asn Gly His
                115                 120                 125

Phe Ser Phe Gly Ile Lys Thr Leu Ile Thr Asn Ser Ser Gln Pro Asn
    130                 135                 140

Val Ile Glu Thr Asp Phe Gly Thr Ala Thr Ala Thr Gln Arg Leu Thr
145                 150                 155                 160

Ile Glu Gly Val Thr Asn Thr Glu Thr Gly Gln Ile Glu Arg Asp Tyr
                    165                 170                 175

Pro Phe Phe Tyr Lys Val Gly Asp Leu Ala Gly Glu Ser Asn Gln Val
                180                 185                 190

Arg Trp Phe Leu Asn Val Asn Leu Asn Lys Ser Asp Val Thr Glu Asp
    195                 200                 205

Ile Ser Ile Ala Asp Arg Gln Gly Ser Gly Gln Gln Leu Asn Lys Glu
    210                 215                 220

Ser Phe Thr Phe Asp Ile Val Asn Asp Lys Glu Thr Lys Tyr Ile Ser
225                 230                 235                 240

Leu Ala Glu Phe Glu Gln Gln Gly Tyr Gly Lys Ile Asp Phe Val Thr
                245                 250                 255

Asp Asn Asp Phe Asn Leu Arg Phe Tyr Arg Asp Lys Ala Arg Phe Thr
                260                 265                 270

Ser Phe Ile Val Arg Tyr Thr Ser Thr Ile Thr Glu Ala Gly Gln His
    275                 280                 285

Gln Ala Thr Phe Glu Asn Ser Tyr Asp Ile Asn Tyr Gln Leu Asn Asn
    290                 295                 300

Gln Asp Ala Thr Asn Glu Lys Asn Thr Ser Gln Val Lys Asn Val Phe
305                 310                 315                 320

Val Glu Gly Glu Ala Ser Gly Asn Gln Asn Val Glu Met Pro Thr Glu
                325                 330                 335

Glu Ser Leu Asp Ile Pro Leu Glu Thr Ile Asp Glu Trp Glu Pro Lys
                340                 345                 350

Thr Pro Thr Ser Glu Gln Ala Thr Glu Thr Ser Glu Lys Thr Asp Thr
    355                 360                 365

Thr Glu Thr Ala Glu Ser Ser Gln Pro Glu Val His Val Ser Pro Thr
    370                 375                 380

Glu Glu Glu Asn Pro Asp Glu Gly Glu Thr Leu Gly Thr Ile Glu Pro
385                 390                 395                 400

Ile Ile Pro Glu Lys Pro Ser Val Thr Thr Glu Glu Asn Gly Thr Thr
                405                 410                 415

Glu Thr Ala Glu Ser Ser Gln Pro Glu Val His Val Ser Pro Thr Glu
                420                 425                 430

Glu Glu Asn Pro Asp Glu Ser Glu Thr Leu Gly Thr Ile Glu Pro Ile
                435                 440                 445

Ile Pro Glu Lys Pro Ser Val Thr Thr Glu Glu Asn Gly Thr Thr Glu
    450                 455                 460

-continued

```
Thr Ala Glu Ser Ser Gln Pro Glu Val His Val Ser Pro Ala Glu Glu
465                 470                 475                 480

Glu Asn Pro Asp Glu Ser Glu Thr Leu Gly Thr Ile Leu Pro Ile Leu
            485                 490                 495

Pro Glu Lys Pro Ser Val Thr Thr Glu Glu Asn Gly Thr Thr Glu Thr
        500                 505                 510

Ala Glu Ser Ser Gln Pro Glu Val His Val Ser Pro Thr Glu Glu Glu
    515                 520                 525

Asn Pro Asp Glu Ser Glu Thr Leu Gly Thr Ile Ala Pro Ile Ile Pro
    530                 535                 540

Glu Lys Pro Ser Val Thr Thr Glu Glu Asn Gly Ile Thr Glu Thr Ala
545                 550                 555                 560

Glu Ser Ser Gln Pro Glu Val His Val Ser Pro Thr Lys Glu Ile Thr
                565                 570                 575

Thr Thr Glu Lys Lys Gln Pro Ser Thr Glu Thr Thr Val Glu Lys Asn
                580                 585                 590

Lys Asn Val Thr Ser Lys Asn Gln Pro Gln Ile Leu Asn Ala Pro Leu
            595                 600                 605

Asn Thr Leu Lys Asn Glu Gly Ser Pro Gln Leu Ala Pro Gln Leu Leu
    610                 615                 620

Ser Glu Pro Ile Gln Lys Leu Asn Glu Ala Asn Gly Gln Arg Glu Leu
625                 630                 635                 640

Pro Lys Thr Gly Thr Thr Lys Thr Pro Phe Met Leu Ile Ala Gly Ile
                645                 650                 655

Leu Ala Ser Thr Phe Ala Val Leu Gly Val Ser Tyr Leu Gln Ile Arg
                660                 665                 670

Lys Asn

<210> SEQ ID NO 10
<211> LENGTH: 313
<212> TYPE: PRT
<213> ORGANISM: Artificial Sequence
<220> FEATURE:
<223> OTHER INFORMATION: TMV CP-GGGGS-SpyCatcher His

<400> SEQUENCE: 10

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Gln Val Trp Lys Pro Ser Pro Gln Val Thr Val Arg Phe Pro
    50                  55                  60

Asp Ser Asp Phe Lys Val Tyr Arg Tyr Asn Ala Val Leu Asn Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140
```

```
Phe Glu Ser Ser Ser Gly Leu Val Trp Thr Ser Gly Pro Ala Thr Gly
145                 150                 155                 160

Gly Gly Gly Ser Gly Gly Gly Ser Gly Gly Gly Ser Met Ser
            165                 170                 175

Tyr Tyr His His His His His Asp Tyr Asp Ile Pro Thr Thr Glu
        180                 185                 190

Asn Leu Tyr Phe Gln Gly Ala Met Val Asp Thr Leu Ser Gly Leu Ser
            195                 200                 205

Ser Glu Gln Gly Gln Ser Gly Asp Met Thr Ile Glu Glu Asp Ser Ala
        210                 215                 220

Thr His Ile Lys Phe Ser Lys Arg Asp Glu Asp Gly Lys Glu Leu Ala
225                 230                 235                 240

Gly Ala Thr Met Glu Leu Arg Asp Ser Ser Gly Lys Thr Ile Ser Thr
            245                 250                 255

Trp Ile Ser Asp Gly Gln Val Lys Asp Phe Tyr Leu Tyr Pro Gly Lys
            260                 265                 270

Tyr Thr Phe Val Glu Thr Ala Ala Pro Asp Gly Tyr Glu Val Ala Thr
        275                 280                 285

Ala Ile Thr Phe Thr Val Asn Glu Gln Gly Gln Val Thr Val Asn Gly
        290                 295                 300

Lys Ala Thr Lys Gly Asp Ala His Ile
305                 310

<210> SEQ ID NO 11
<211> LENGTH: 193
<212> TYPE: PRT
<213> ORGANISM: Artificial Sequence
<220> FEATURE:
<223> OTHER INFORMATION: TMV CP-GGGGS-SpyTag His

<400> SEQUENCE: 11

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Gln Val Trp Lys Pro Ser Pro Gln Val Thr Val Arg Phe Pro
    50                  55                  60

Asp Ser Asp Phe Lys Val Tyr Arg Tyr Asn Ala Val Leu Asn Pro Leu
65                  70                  75                  80

Val Thr Ala Leu Leu Gly Ala Phe Asp Thr Arg Asn Arg Ile Ile Glu
            85                  90                  95

Val Glu Asn Gln Ala Asn Pro Thr Thr Ala Glu Thr Leu Asp Ala Thr
        100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Gly Pro Ala Thr Gly
145                 150                 155                 160

Gly Gly Gly Ser Gly Gly Gly Ser Gly Gly Gly Ser Ala His
            165                 170                 175
```

Ile Val Met Val Asp Ala Tyr Lys Pro Thr Lys His His His His
            180                 185                 190

His

<210> SEQ ID NO 12
<211> LENGTH: 169
<212> TYPE: PRT
<213> ORGANISM: Artificial Sequence
<220> FEATURE:
<223> OTHER INFORMATION: 11-20 SpyCatcher

<400> SEQUENCE: 12

Met Ser Tyr Tyr His His His His His Asp Tyr Asp Ile Pro Thr
1               5                   10                  15

Thr Glu Asn Leu Tyr Phe Gln Gly Ala Met Val Asp Thr Leu Ser Gly
                20                  25                  30

Leu Ser Ser Glu Gln Gly Gln Ser Gly Asp Met Thr Ile Glu Glu Asp
            35                  40                  45

Ser Ala Thr His Ile Lys Phe Ser Lys Arg Asp Glu Asp Gly Lys Glu
        50                  55                  60

Leu Ala Gly Ala Thr Met Glu Leu Arg Asp Ser Ser Gly Lys Thr Ile
65                  70                  75                  80

Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Lys Ala Thr Lys Gly Asp Ala His Ile Leu Asp Ile Val Ala
130                 135                 140

Asp Ile Asn Gly Val Gln Ile Glu Val Pro Ile Leu Pro Thr Thr Lys
145                 150                 155                 160

Ala Lys Ile Ile Ala Lys Ile Ile Gly
                165

<210> SEQ ID NO 13
<211> LENGTH: 358
<212> TYPE: PRT
<213> ORGANISM: Artificial Sequence
<220> FEATURE:
<223> OTHER INFORMATION: GalEst

<400> SEQUENCE: 13

Met His His His His His Ala His Ile Val Met Val Asp Ala Tyr
1               5                   10                  15

Lys Pro Thr Lys Met Arg Val Leu Val Thr Gly Gly Ser Gly Tyr Ile
                20                  25                  30

Gly Ser His Thr Cys Val Gln Leu Leu Gln Asn Gly His Asp Val Ile
            35                  40                  45

Ile Leu Asp Asn Leu Cys Asn Ser Lys Arg Ser Val Leu Pro Val Ile
        50                  55                  60

Glu Arg Leu Gly Gly Lys His Pro Thr Phe Val Glu Gly Asp Ile Arg
65                  70                  75                  80

Asn Glu Ala Leu Met Thr Glu Ile Leu His Asp His Ala Ile Asp Thr
                85                  90                  95

Val Ile His Phe Ala Gly Leu Lys Ala Val Gly Glu Ser Val Gln Lys
            100                 105                 110

-continued

```
Pro Leu Glu Tyr Tyr Asp Asn Val Asn Gly Thr Leu Arg Leu Ile
        115                 120                 125

Ser Ala Met Arg Ala Ala Asn Val Lys Asn Phe Ile Phe Ser Ser Ser
130                 135                 140

Ala Thr Val Tyr Gly Asp Gln Pro Lys Ile Pro Tyr Val Glu Ser Phe
145                 150                 155                 160

Pro Thr Gly Thr Pro Gln Ser Pro Tyr Gly Lys Ser Lys Leu Met Val
                165                 170                 175

Glu Gln Ile Leu Thr Asp Leu Gln Lys Ala Gln Pro Asp Trp Ser Ile
                180                 185                 190

Ala Leu Leu Arg Tyr Phe Asn Pro Val Gly Ala His Pro Ser Gly Asp
        195                 200                 205

Met Gly Glu Asp Pro Gln Gly Ile Pro Asn Asn Leu Met Pro Tyr Ile
        210                 215                 220

Ala Gln Val Ala Val Gly Arg Arg Asp Ser Leu Ala Ile Phe Gly Asn
225                 230                 235                 240

Asp Tyr Pro Thr Glu Asp Gly Thr Gly Val Arg Asp Tyr Ile His Val
                245                 250                 255

Met Asp Leu Ala Asp Gly His Val Val Ala Met Glu Lys Leu Ala Asn
                260                 265                 270

Lys Pro Gly Val His Ile Tyr Asn Leu Gly Ala Gly Val Gly Asn Ser
        275                 280                 285

Val Leu Asp Val Val Asn Ala Phe Ser Lys Ala Cys Gly Lys Pro Val
        290                 295                 300

Asn Tyr His Phe Ala Pro Arg Arg Glu Gly Asp Leu Pro Ala Tyr Trp
305                 310                 315                 320

Ala Asp Ala Ser Lys Ala Asp Arg Glu Leu Asn Trp Arg Val Thr Arg
                325                 330                 335

Thr Leu Asp Glu Met Ala Gln Asp Thr Trp His Trp Gln Ser Arg His
                340                 345                 350

Pro Gln Gly Tyr Pro Asp
        355
```

NANONETS AND SPHERICAL PARTICLES

CROSS REFERENCE TO RELATED APPLICATIONS

This application is a 371 National Stage entry of International Application No. PCT/GB2018/051495 with an international filing date of May 31, 2018, which claims the benefit of priority to Great Britain Application No. 1708675.2 filed on May 31, 2017, the entire contents of each of which are herein incorporated by reference in their entirety for all purposes.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named P184655_SEQUENCE_ST25.TXT, created on Nov. 27, 2019, and having a size of 29 kilobytes and is filed concurrently with the specification. The sequence listing contained in this ASCII formatted document is part of the specification and is herein incorporated by reference in its entirety.

FIELD OF THE INVENTION

The present invention relates to macromolecular complexes comprising micron-scale networks which include binding motifs thereon which allow the covalent bonding of the micron-scale networks to particles which provide nanoscale display surfaces. Further, the present invention provides for the synthesis of nano-, micro-scale functional materials, in particular synthesis of such materials without the need to use complex and restrictive linker chemistries.

BACKGROUND OF THE INVENTION

One of the major goals of material science is to produce materials that are ordered on all length scales, from molecular (1-100 Å), nano (10-100 nm) to macro (1-100 micron). The development of systems with integrated catalytically active enzymes, specific antibodies or other biologics have high potential for synthesis, degradation and biosensor diagnostics of various biologically active substances.

It has been demonstrated that short peptide sequences can be incorporated into different regions of the coat proteins of virus or virus like particles (VLP—virus which does not include nucleic acid), for example at the C-termini, such that the peptides are surface displayed on the VLP after self-assembly; conferring surface functionality of interest. However, this system for surface display is limited by the size of the peptide that can be inserted.

Alternatively, functionalization may be achieved by chemical linkage approaches, whereby larger proteins and peptides may be covalently linked to addressable amino acids on the surface of a VLPs (for example carbodiimide crosslinking of carboxyl to amine groups) or by non-specific crosslinking reactions (glutaraldehyde). Additionally, these chemical linkage approaches have been used to create linkages between surface functionalized viruses/VLPs for the production of macroscale scaffolds with multienzyme utility.

However, a disadvantage of chemical linkage approaches is that they may provide too much non-specific cross-linkage which may reduce peptide/protein reactivity, or alternatively/additionally there may be the requirement for additional clean up steps. Thus, alternative strategies are required. WO2014/113203 discusses this problem and proposes asymmetrically functionalised virus particles and linker molecules made up of a long hydrophilic carbon chain or hydrophilic polymer.

WO2016/112921 discusses antigen array display scaffolds provided to spherical VLPs of a size 22 to 150 nm which appears optimal for efficient uptake by professional antigen presenting cells. In particular WO2016/112921 discusses the modification of the AP205 capsid protein to include a 116 amino acid SpyCatcher polypeptide and the production of antigens fused to a SpyTag polypeptide. The antigen can then be coupled to the AP205 capsid protein surface.

SUMMARY OF THE INVENTION

The present inventors have determined that virus and virus like particles that are able to assemble into micron structures can be modified to include a peptide tag or a binding protein of a peptide tag and binding protein pair wherein the peptide tag and binding protein pair are capable of spontaneously forming a covalent bond, for example an isopeptide bond, to provide functionalised micron-structures. Advantageously, the method provides for a 'one-pot' conjugation step rather than more complex chemical approaches that typically require clean up steps.

Accordingly, a first aspect of the present invention provides a macromolecular complex comprising:
(i) a micron-structure comprising a first member of a covalently reactive peptide tag and binding protein pair wherein the peptide tag and binding protein pair are capable of spontaneously forming a covalent bond,
(ii) a nanoscale display surface comprising a second member of a covalently reactive peptide tag and binding protein pair that is capable of binding the first member of (i) to spontaneously form a covalent bond.

The micronscale network provided by the invention may suitably be spontaneously formed. Suitably a macroscale network structure may be provided for example using a modified TMV coat protein (suitably provided by amino acid changes in the TMV to allow assembly without the presence of nucleic acid and including SpyTag or Spy-Catcher). Such a micron macroscale structure provides a porous structure. Suitably there is provided a first complex comprising a self-assembled macromolecular network micron-structure derived from virus components which surface displays a motif that can spontaneously form covalent linkages with a second complex comprising a fluorescent particle wherein the fluorescent particle surface displays the motif interacting partner. Such macroscale structures comprising a fluorescent nano-display surface comprise a non-viral component.

Suitably, TMV coat protein, modified with a peptide tag or binding protein of a peptide tag (for example SpyTag or SpyCatcher) does not form spherical particles, but spontaneously forms micron-sized porous network structures which are larger than individual VLPs.

Suitably the covalent bond spontaneously formed may be an isopeptide bond between a peptide tag and a binding protein of a peptide tag and binding protein pair.

In embodiments the micron-structure can comprise a self-assembled macromolecular network structure derived from virus components. The virus components of the micron-structure can be the same or different to each other. Suitably the virus components may be selected from a virus coat protein or virus like particle. Suitably the virus coat protein or virus like particle can form networks of rods or, when expressed at high levels, aggregates of micron scale.

Various modified TMV coat protein constructs with peptide tag or a binding protein of a peptide tag (e.g. SpyTag or SpyCatcher) introduced into the expressed coat protein have been produced, expressed, and tested under multiple isolation conditions. The TMV constructs have produced micron-scale networks rather than distinct 18 nm rods of different length which would be expected if SpyTag or SpyCatcher were not included. Without wishing to be bound by theory, the inventors consider that high levels of expression of coat proteins which can't fold or assemble in the appropriate manner due to an introduced tag or binding protein may be provided during expression of a construct. Partial or aborted assembly may lead to aggregates in the form of networks. It is considered that further types of VLP or virus coat protein depending on the size of the insert and insertion in the coat protein sequence would cause aggregates to form.

Suitably, such virus component or virus like particles may be provided by a rod-shaped virus. Suitably the virus component or virus like particle may be provided by the rod-shaped tobacco mosaic virus (TMV), tobacco rattle virus (TRV), spherical brome mosaic virus, cowpea mosaic virus (CPMV), cowpea chlorotic mottle virus or filamentous potato virus X (PVX). Alternatively, suitably components or virus like particles may be provided by bacteriophages such as M13, T4, T7, lambda or MS2.

Advantageously, these components or virus like particles can be obtained to high yields. Further, advantageously coat proteins (CPs) or other components (not limited to phage tail fibres, or plant virus movement proteins) can be manipulated to surface display peptides, proteins and/or enzymes which confer high catalytic/reactive activities of interest to the virion or structures surface. In a suitable advantageous embodiment, surface display of peptides/proteins/enzymes on characterised coat proteins for example, can greatly enhance the stability of the enzymes/proteins and permit provision of very dense reactive surface areas after self-assembly.

To maintain biocontainment either a virus can be rendered non-replicative, or alternatively virus-like particles (VLPs) produced from self-assembled coat proteins which lack infectious nucleic acid can be used. Given that VLPs can be readily produced from the coat proteins of many viruses and be isolated to high yield with no containment issues, they combine the features of safety and commercial viability. While some virus coat proteins can be expressed which spontaneously self-assemble into VLP structures without any requirement for the viral nucleic acid, others like tobacco mosaic virus (TMV), a major "workhorse" for nanobiotechnology (due to its genetic malleability and stability to temperatures up to 60° C. and pH ranges of 2-9) are considered to require either defined buffering conditions or genetic modification of the CP in order to assemble without nucleic acid. The latter approach is likely more commercially feasible due to less downstream processing and greater particle uniformity.

Wildtype TMV exists as 300 nm length, 18 nm diameter rods formed from 2130 identical coat protein subunits which encapsidate a plus-sense single stranded RNA genome of 6395 nucleotides. Assembly of TMV coat protein (CP) monomers into this structure requires RNA and the presence of cations in order to counteract the flanking repulsive negative charges between the CP subunits that are detrimental to oligomerization. Suitably, a VLP can be provided which includes mutations at E50Q and D77N in the CP sequence to effectively remove the repulsive groups and enable self-assembly of the CP monomers into a TMV rod like structure in the absence of nucleic acid, and when expressed in bacteria the modified CP produce RNA free TMV VLP rods of variable length. Suitably subsequent addition of a protein or "peptide tag" or further changes to the CP sequence, for example inclusion of a binding protein of a peptide tag, or bacterial induction conditions, or purification conditions may provide coat protein which can spontaneously form self assembled macromolecular micron scale network structures.

The TMV coat protein only poorly assembles without nucleic acid in the presence of cations. Mutations at E50Q and D77N overcome this limitation by replacing repulsive charges which prevent interaction between neighbouring coat proteins. This is considered to allow formation of rods which are 18 nm in diameter but can be up to several microns in length (since RNA is not present to dictate the length of 300 nm). Upon insertion of SpyCatcher, SpyTag and/or linker sequences at the C-terminal end of the E50Q D77N mutated coat protein, micronscale networks rather than distinct rods have been determined to form.

These network structures may provide the desired surface displayed functionalities being contingent upon the nature of the introduced groups; these micron scale structures may or may not be composed of obvious discrete VLPs, but may comprise aggregates of the coat protein, for example as discussed Love A., Makarov V., Sinitsyna O., Shaw J., Yaminsky I., Kalinina N., Taliansky M., A genetically modified tobacco mosaic virus that can produce gold nanoparticles from a metal salt precursor. Frontiers in Plant Science, 2015, 6, 984 doi.org/10.3389/fpls.2015.00984.

As used herein, the term "peptide tag" generally refers to a small peptide fragment, suitably 5 to 50 amino acids in length, for example 10, 20, 30, 40 or 50 amino acids in length, which may be fused to another peptide or protein, for example a VLP or a self assembled micron scale network, that may or may not be designed or derived directly from an isopeptide protein. The term "binding partner" is a protein which can form an isopeptide bond to the "peptide tag".

In embodiments the covalently reactive peptide tag and binding protein pair can comprise SpyCatcher/SpyTag, SnoopCatcher/SnoopTag, the *Streptococcus pyogenes* split pilin N-terminal isopeptide tag/the *Streptococcus pyogenes* split pilin C-terminal isopeptide tag, or other peptide tag and protein binding pairs which provide for spontaneous formation of isopeptide bonds, for example between a between carboxyl/carboxamide and amino groups, suitably a lysine and an asparagine residue. Suitably, the covalently reactive peptide tag and binding protein pair may comprise SpyCatcher/SpyTag, SnoopCatcher/SnoopTag, the *Streptococcus pyogenes* split pilin N-terminal isopeptide tag/the *Streptococcus pyogenes* split pilin C-terminal isopeptide tag.

Suitably, the tag may be about 5 to 15 amino acids in length. Suitably, the tag or binding protein may not affect the biologically activity of the micron-structure or nanoscale display surface to which it is provided.

In embodiments the first member of the covalently reactive peptide tag and binding protein pair comprises a tag, for example SpyTag, SnoopTag or the *Streptococcus pyogenes* split pilin C-terminal isopeptide tag, ACE19—a domain of adhesion protein from *E. faecalis* which spontaneously forms an isopeptide bond, the collagen binding domain from *S. aureus* which forms an isopeptide bond, FbaB from *Streptococcus pyogenes* comprising a domain CnaB2, and bacteriophage HK97 subunits which spontaneously form isopeptide bonds. WO2011/098772 discusses such tags and binding protein pairs. Further examples of covalently reactive peptide tag and binding protein pair comprise homologues, for example with at least 70%, at least 80%, at least 90%, at least 95%, at least 99% sequence identity to the tag or binding protein discussed above or mutants of proteins capable of spontaneously forming one or more isopeptide bond, for example wherein the covalently reactive peptide tag and binding protein pairs discussed herein are mutated via insertion, deletion, or substitution of one more than one, for example, 2, 3, 4, 5, 6, 7, 8, 9 or 10 amino acid residues from the wild type residues (known or published sequences) of a peptide tag and binding protein pair which can spontaneously form an isopeptide bond. Suitably a mutation may be within 5 to 10 amino acids of the amino acids which form the isopeptide bond. Suitably, a mutation may be provided by substituting an amino acid(s) with an amino acid with similar properties, for example similar hydrophobicity, charge, size of side chain. Mutants which retain the ability to form an isopeptide bond can be determined using computer software or via for example phage display screening techniques.

Amino acid identity can determined by methods and computer programs as known in the art, for example using the local homology algorithm of Smith and Waterman with the default values. Software for providing such analysis is publicly available through the national Center for Biotechnology Information.

In embodiments the second member of the covalently reactive peptide tag and binding protein pair comprises a SpyCatcher, SnoopCatcher, or the *Streptococcus pyogenes* split pilin N-terminal isopeptide tag.

In embodiments the micron-structure can comprise a combination of first members of different covalently reactive peptide tags and binding protein pairs wherein the respective peptide tag and binding protein pair are capable of spontaneously forming a covalent bond and a nanoscale display surface can comprise a combination of second members of different covalently reactive peptide tag and binding protein pairs that are respectively capable of binding to the corresponding first member to spontaneously form a covalent bond.

In embodiments a nanoscale display surface can be a nucleic acid molecule, protein, enzyme, peptide, polysaccharide, small molecule, metal-ligand complex, nanoparticle, nanotube or polymer. In embodiments, the nanoscale display surface can be a fluorescent label, a luminescent label, or chromophore. In embodiments, a nanoscale display surface comprising a second member of a covalently reactive peptide tag and binding protein can comprise a fluorescent protein, suitably selected from GFP, CFP, RFP, YFP, mCherry, iLOV or cerulean or fragments or biologically active derivatives thereof (for example cerulean fluorescent protein and yellow fluorescent protein can be obtained from GFP via a few amino acid changes). In embodiments, multiple fluorescent proteins may be conjoined together to form nanoscale display surfaces. Suitably fluorescent proteins as would be known in the art are discussed, for example by Rebekka M Wachter, Marc-André Elsliger, Karen Kallio, George T Hanson and S James Remington; "Structural basis of spectral shifts in the yellow-emission variants of green fluorescent protein"; Structure 15 Oct. 1998, 6:1267-1277 [2] Mats Ormo, Andrew B. Cubitt, Karen Kallio, Larry A. Gross, Roger Y. Tsien, S and James Remington; "Crystal Structure of the *Aequorea Victoria* Green Fluorescent Protein", Science (273) September 1996 5280, 1392-1396 and Brian G. Reid and Gregory C. Flynn; "Chromophore Formation in Green Fluorescent Protein"; Biochemistry 1997, 36, 6786-6791, and further by Wachter, King, Heim, Kallio, Tsien, Boxer and Remington; "Crystal Structure and Photodynamic behaviour of the blue emission variant Y66H/Y145F of Green.

In an embodiment, the inventors have modified the tobacco mosaic virus (exists as a 18 nm×300 nm rod) coat protein to form micron-scale networks which lack nucleic acid and which also surface display SpyTags (a peptide tag which binds covalently to a SpyCatcher protein via an amide bond (Zakeri, Bijan; Fierer, Jacob O.; Celik, Emrah; Chittock, Emily C.; Schwarz-Linek, Ulrich; Moy, Vincent T.; Howarth, Mark (2012). "*Peptide tag forming a rapid covalent bond to a protein, through engineering a bacterial adhesin*". Proceedings of the National Academy of Sciences. 109 (12): E690-7)).

Further, the inventors have created nanoscale spherical Green Fluorescent Protein (GFP) particles which contain SpyCatcher motifs which can covalently bond to the SpyTags on the surface of the micron-scale networks. Such binding leads to robust and rapid decoration of these networks with spherical particles of GFP.

Each of the
(i) a micron-structure comprising a first member of a covalently reactive peptide tag and binding protein pair wherein the peptide tag and binding protein pair are capable of spontaneously forming a covalent bond, and
(ii) a nanoscale display surface comprising a second member of a covalently reactive peptide tag and binding protein pair that is capable of binding the first member of (i) to spontaneously form a covalent bond
are considered to provide separate aspects of the present invention.

Further, the inventors have developed a "one pot" synthesis of nano-, micro-scale functional materials, whereby, for example proteins or enzymes of any description may be attached to either the micron-structure (for example VLP or other virus derived self-assembled structure) or the nanoscale display surface (for example GFP spherical particles) via covalent interaction, suitably a spontaneously forming isopeptide bond, for example via SpyTag/SpyCatcher interaction, SnoopCatcher, or the *Streptococcus pyogenes* split pilin N-terminal isopeptide tag. Suitably the synthesis is relatively rapid. Suitably the synthesis does not require complex and restrictive linker chemistries. Accordingly, this provides a separate aspect of the present invention.

The micron-structure of (i) or a nanoscale display surface (ii) of the invention may be provided by chemical synthesis or recombinant cells.

Suitably, there is provided a vector comprising a nucleic acid sequence encoding a micron-structure of (i) or a nanoscale display surface (ii) the invention. The vector may include a control sequence operably linked to the tag and or binding protein. Suitably the control sequence can comprise a promoter, enhancer, transcription initiation site, termination site, or a combination of thereof. The vector may further comprise a selective marker gene or means to aid the incorporation of the nucleic acid into a cell, or the transcription or expression of the nucleic acid into the cell.

Suitably, the present invention provides a kit comprising at least one of (i) a micron-structure comprising a first member of a covalently reactive peptide tag and binding protein pair wherein the peptide tag and binding protein pair are capable of spontaneously forming a covalent bond, and (ii) a nanoscale display surface comprising a second member of a covalently reactive peptide tag and binding protein pair that is capable of binding the first member of (i) to spontaneously form a covalent bond. Suitably the kit may comprise a vector(s) able to express at least one of (i) a micron-structure comprising a first member of a covalently reactive peptide tag and binding protein pair wherein the peptide tag and binding protein pair are capable of spontaneously forming a covalent bond, and (ii) a nanoscale display surface comprising a second member of a covalently reactive peptide tag and binding protein pair that is capable of binding the first member of (i) to spontaneously form a covalent bond. Suitably the kit may further comprise cells into which the vector may be introduced. Suitably the kit may comprise cells transformed with a vector or vectors of the invention.

In embodiments a nucleic acid sequence encoding the peptide tag or binding partner may be operable linked to respective control sequences in a vector of interest, for example to express a VLP (or a self assembling virus derived component which may form a VLP and/or micron scale network) and tag, or to express a fluorescent protein and binding protein.

It is considered the development of biomimetic 2d and 3d nanodevices and nanomaterials from virus and other protein nanoparticles have potential applications in medicine, veterinary medicine, agriculture and biocatalysis.

The SpyTag/SpyCatcher system has been developed from the collagen adhesion domain of *Streptococcus pyogenes*, in particular the SpyTag (13 amino acids) peptide can form a covalent isopeptide bond with its interacting partner, namely the SpyCatcher (116 amino acids) peptide. This bond formation is typically spontaneously rapid and specific. This bond formation reaction can occur in diverse conditions and is relatively unaffected by temperature and pH variation. Moreover, it is believed that bond formation can occur with SpyCatcher irrespective of whether the SpyTag is located in the N-, C-termini or central regions of the host protein.

In an embodiment of the present invention, SpyTag can be introduced into the C-terminal end of an E50Q and D77N modified TMV CP. Suitably, the modified TMV CP may be expressed in bacteria. It was expected that this would form discrete 18 nm rods of varying length; however surprisingly it was determined that large macromolecular networks were obtained.

To demonstrate the SpyTag was surface displayed on this macroscale structure, the 116 amino acid SpyCatcher sequence was fused to the N-terminal end of GFP in order to test the interaction between the SpyCatcher-GFP with the TMV CP-SpyTag network.

When expressed alone, the SpyCatcher-GFP unexpectedly formed fluorescent 50-100 nm spherical particles. These particles did not include a long C-terminal extension which has previously been indicated as being required for formation of fluorescent spherical particles.

When both the SpyTag displayed macroscale structure was incubated with the SpyCatcher-GFP particles, they formed rapid covalent bonds mediated via the interaction of the SpyCatcher with its SpyTag partner. This confirmed that both respective Spy components were surface displayed and capable of forming a covalent interaction. It is considered that virus derived macromolecular complexes provide a macroscale platform on which nanoscale display particles, for example SpyCatcher-GFP particles can be provided for the rapid surface presentation of proteins (or potential enzymes) of interest.

Suitably, a macroscale network may be derived from TMV coat proteins or TMV VLPs assembled from coat proteins. In embodiments the macroscale network can be formed from a microstructure comprising viral coat proteins or VLPs, suitably, wherein the viral coat proteins may comprise motifs which allow the viral coat proteins or VLPs to coalesce to form networks. The networks formed may not appear to comprise obvious virus like particles and may appear to be aggregated strings of coat proteins. These networks may be formed by at least one of insertion of amino acid sequences or motifs into the coat protein, induction of bacterial expression and protein isolation. Suitably such structures may be modified by introducing a SpyTag into the C-terminal end of the TMV CP. Advantageously, introduction of a SpyTag into the C-terminal end of the TMV-CP may provide large TMV network structures (devoid of nucleic acid), when expressed in bacteria. SpyTag at the C-terminal end of TMV CP can suitably form covalent linkages with its SpyCatcher interacting partner which may be suitably surface displayed on GFP spherical particles. Suitably networks, including SpyTag, may be decorated with surface displayed SpyCatcher, for example GFP spherical particles to provide different functional proteins (or enzymes), effectively producing bioactive 2d/3d macroscale nanomaterials.

In embodiments larger micronscale networks can be created by combining two populations of SpyTag TMV derived networks and utilizing a SpyCatcher linker to join the two networks together. Alternatively SpyTag networks could be mixed with SpyCatcher networks, to form larger network structures. As will be appreciated, a combination of peptide tags and binding proteins to respective peptide tags may be used to allow multiple microscale networks to be combined to form larger structures/networks. Details of further peptide tags and binding proteins which may be used for example in combination with each other or with SpyTag and SpyCatcher are provided below.

The SnoopTag/SnoopCatcher system was developed from the RrgA adhesin from *Streptococcus pneumoniae*, where the SnoopTag constitutes residues 734-745, and the SnoopCatcher constitutes residues 749-860. The system was further optimized by incorporating mutations at G842T and D848G (Veggiani et al. 2016).

The Isopeptag system was developed from the *Streptococcus pyogenes* major pilin protein by splitting and separating the covalently interacting domains, whereby the N-terminal pilin domain reacts with the split pilin N-terminal isopeptide tag and the split C-terminal domain interacts with the C-terminal isopeptide tag (Veggiani et al. 2016).

In embodiments the covalent linkages/functionalities of the micron-structures or nanoscale display particles may be provided by the insertion of derivatives, components, and sequence elements of these covalent linkage systems into the protein sequences which provide the micron-structures or nanoscale display.

In embodiments, the micron-structure can be provided with more than one covalent linkage systems, for example a virus coat protein, e.g. modified TMV coat protein which can generate micron or macroscale network complexes can be provided with at least two of SpyTag, SnoopTag and a member of the Isopeptag system with isopeptide bonding activity. This can allow selective attachment to particular tags.

In embodiments, the tag or binding protein may be provided to the micro-structure or nanoscale surface display via a linker or spacer. For example a glycine/serine rich spacer may be provided. In embodiments, the spacer may include a site for specific proteolysis to allow release or the binding pair member from the micron-structure.

Suitably, the isopeptide bond may be a chemical bond or a covalent bond which forms between the tag and the binding partner as described herein which can be stable after heating to 70° C., yet more suitably 80° C., yet more suitably 90° C., yet more suitably 95° C. Suitably the bond can form from pH 2 to 10 and in a temperature range from −20° C. to 100° C., suitably 4° C. to 40° C. at a pH in the range from 5 to 8.

In an embodiment a SpyTag/SpyCatcher can be formed from an amino acid sequence as described by NCBI Entrez Code AAK33238 (encoded by nucleic acid described by NCBI Entrez Accession code AE004092) wherein the isopeptide bond is formed between the lysine at position 179 and asparagine 303. Thus the peptide tag preferably comprises the reactive asparagine of position 303 and the binding partner (SpyCatcher) suitably comprises a fragment with the lysine at position 179.

In an embodiment as described herein ACE19, comprising an amino acid sequence as described by NCBI Entrez Accession code NP_814829, and encoded by the nucleic acid sequence described by NCBI Entrez Accession Code NC_004668 can be used wherein the isopeptide bondy occurs between a lysine residue at position 181 and an asparagine residue at position 294. Thus the tag preferably includes the reactive asparagine at position 294 and the binding partner can comprise a fragment comprising the lysine at position 181.

Preferred features and embodiments of each aspect of the invention are as for each of the other aspects mutatis mutandis unless context demands otherwise.

As used herein, the articles "a" and "an" refer to one or to more than one (for example to at least one) of the grammatical object of the article.

"About" shall generally mean an acceptable degree of error for the quantity measured given the nature or precision of the measurements.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Embodiments of the invention will now be described by way of example only, with reference to the accompanying figures.

FIG. 1: (A) Western blot of lysates before and after incubation and after centrifugation on 20% sucrose cushions, probed with a TMV antibody. Molecular weight marker (in kDa) is shown on left-hand side. TMVc denotes TMV CP (E50Q and D77N modified) lysate, TMVc* denotes lysate containing TMVc with inserted C-terminal SpyTag, and GFP+ indicates SpyCatcher-GFP lysates; with TMVc*/GFP+ and TMVc/GFP+ representing mixed incubations of these lysates. #indicates TMVc* bands detected with the TMV antibody. (B) As per (A) except blots were probed with a GFP specific antibody. Molecular weights of TMVc, TMVc* and GFP+ are indicated below Westerns.

Figure 2:
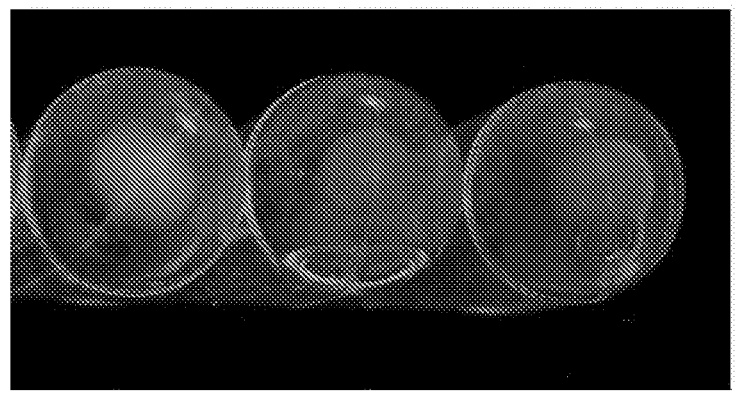

FIG. 2: Centrifuge tubes illuminated under a UV lamp after centrifugation on a 20% sucrose gradient, indicating GFP fluorescence in TMVc*/GFP+, but not in TMVc/GFP+ or GFP+.

Figure 3:
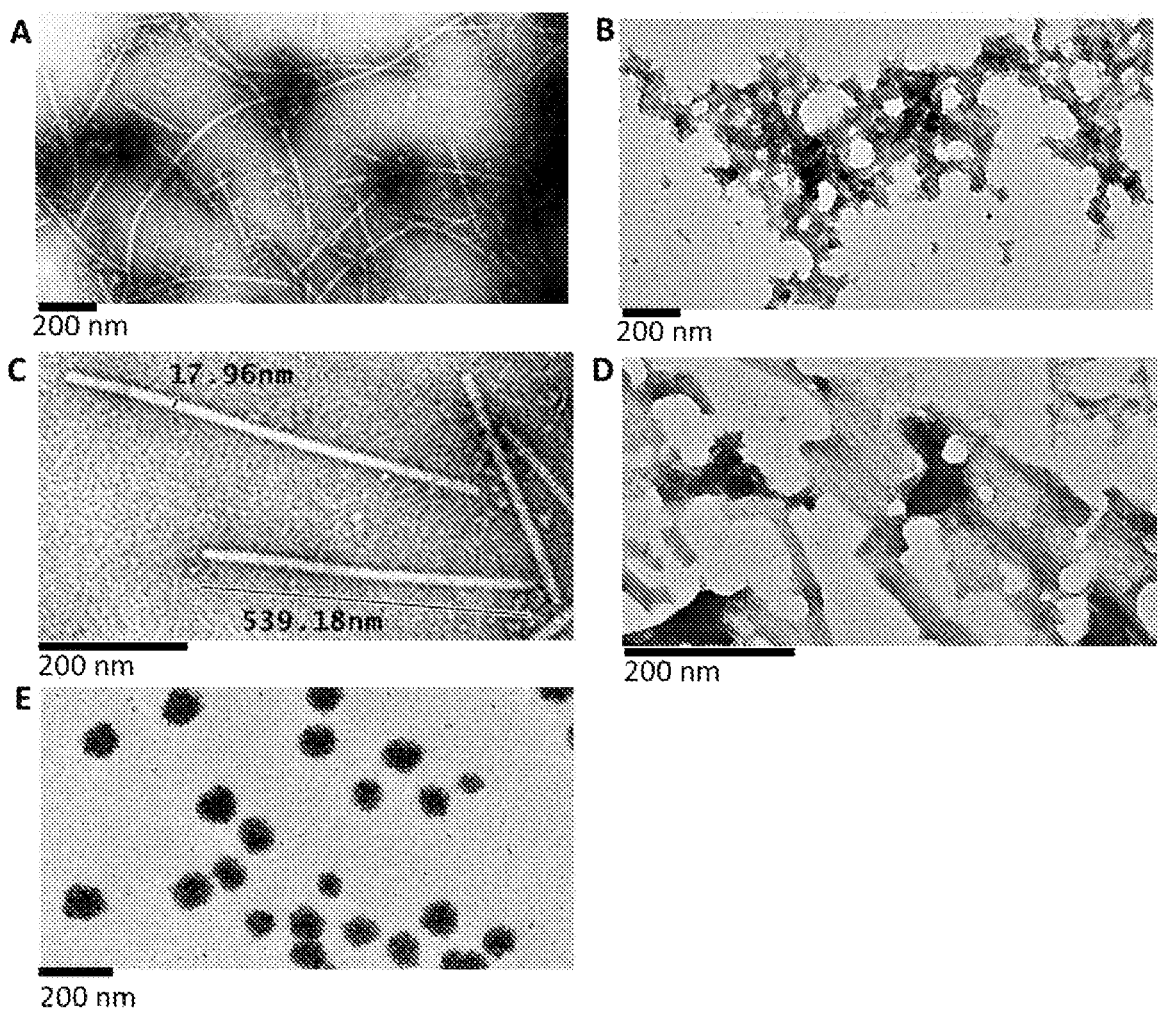

FIG. 3: Transmission electron microscopic imaging of lysates of bacteria expressing TMVc (A and C), TMVc* (B and D) and GFP+ (E). Scale bars are shown.

Figure 4:
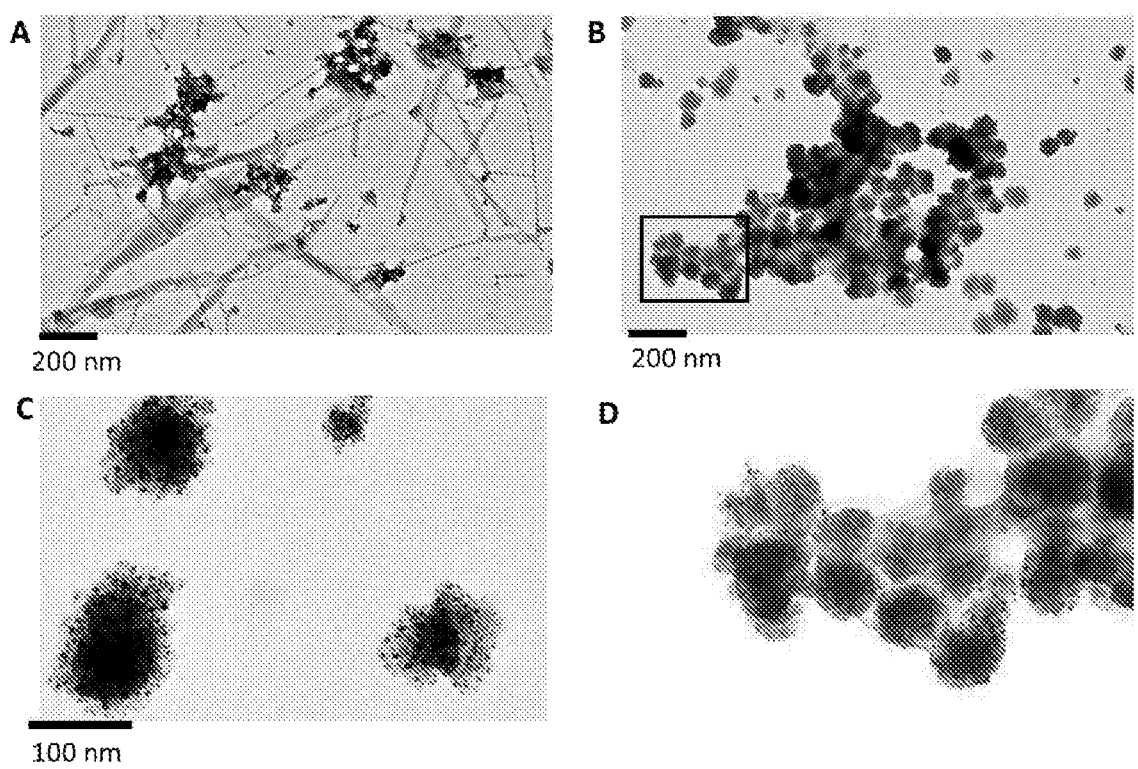

FIG. 4: Transmission electron microscope images of TMVc (A) or TMVc* (B) which have been incubated with GFP+ and then purified from 20% sucrose cushions. The black square in (B) denotes the zoomed in region which is shown in (D). (C) GFP+ particles decorated with gold conjugated GFP antibodies. (D) Close up of (B) showing that the aggregates bind gold conjugated GFP antibodies. Scale bars are shown.

Figure 5:
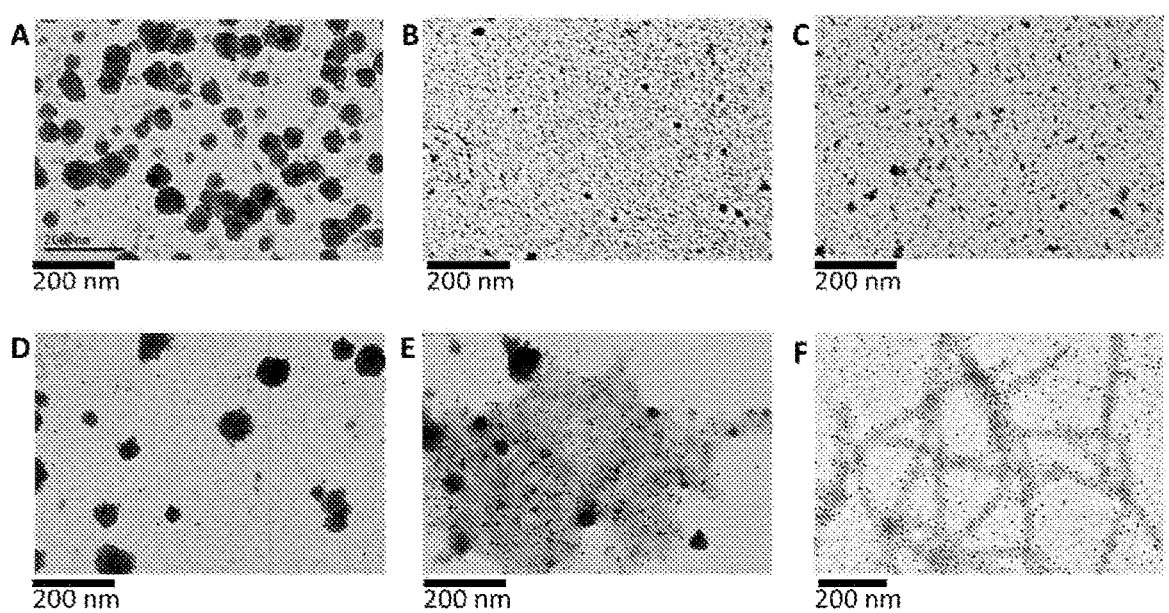

FIG. 5: Transmission electron microscope images of GFP antibody coated grids which can immunocapture GFP+ particles (A) but not TMVc (B) or TMVc* (C), thus indicating specificity of the antibody. Grids with the bound GFP+ were incubated with TMVc (D) or (E) TMVc* and then washed and exposed to gold labelled TMV antibodies. (F) Purified TMVc only can associate with gold labelled TMV antibodies, demonstrating antibody specificity. Scale bars are shown.

Figure 6:
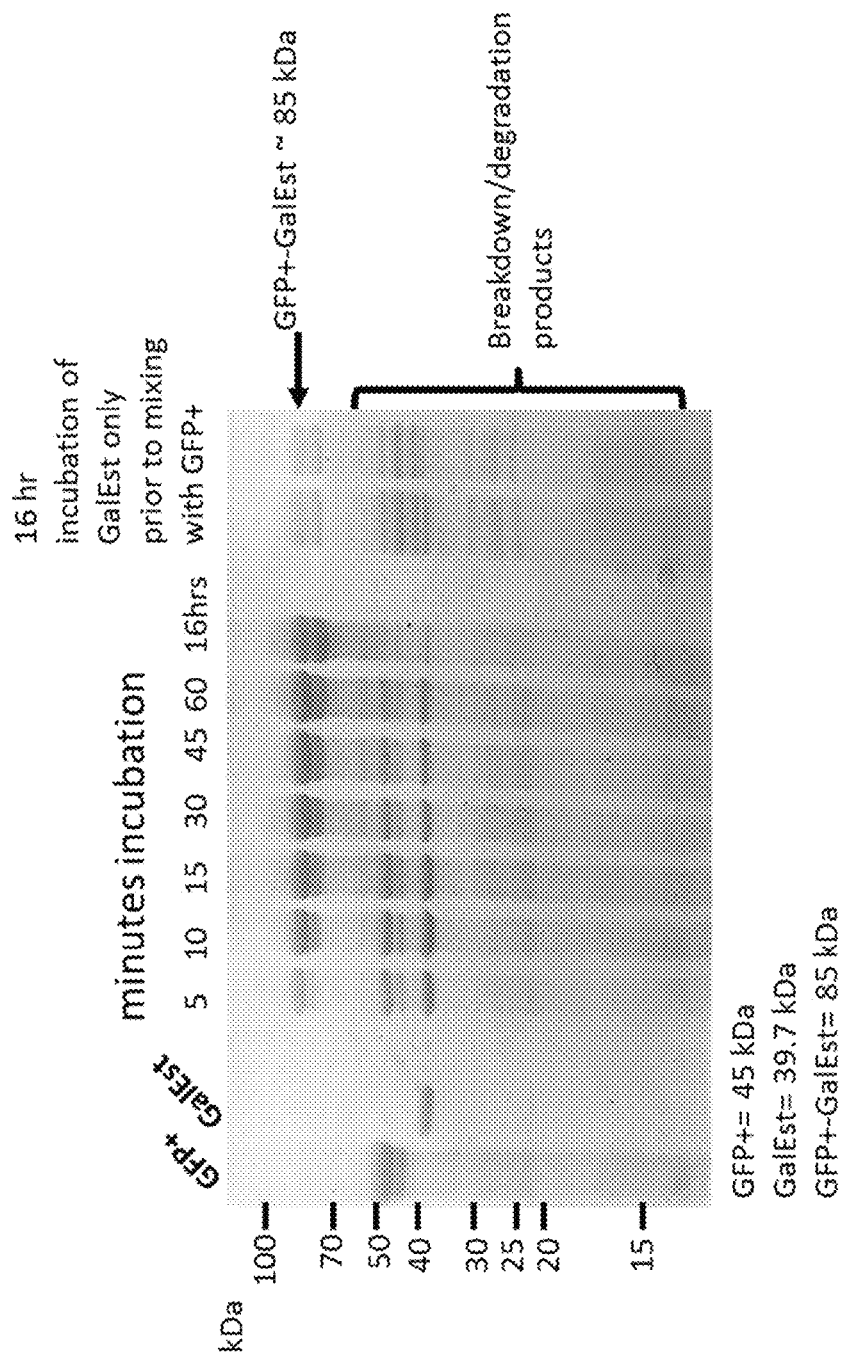

FIG. 6: Coomassie stained SDS-PAGE of uridine 5'-diphosphogalactose 4-epimerase fused to a SpyTag (GalEst), and GFP+ which were isolated from bacteria (lanes marked GFP+ and GalEst), prior to mixing and incubating for 5 minutes till 16 hours (minutes incubation). The two rightmost lanes are a duplicate of GalEst and GFP+ incubated separately for 16 hours prior to mixing before loading. Molecular weight markers are shown on the left-hand side. Molecular weights of GFP+, GalEst and GFP+-GalEst are indicated under the gel.

Figure 7:
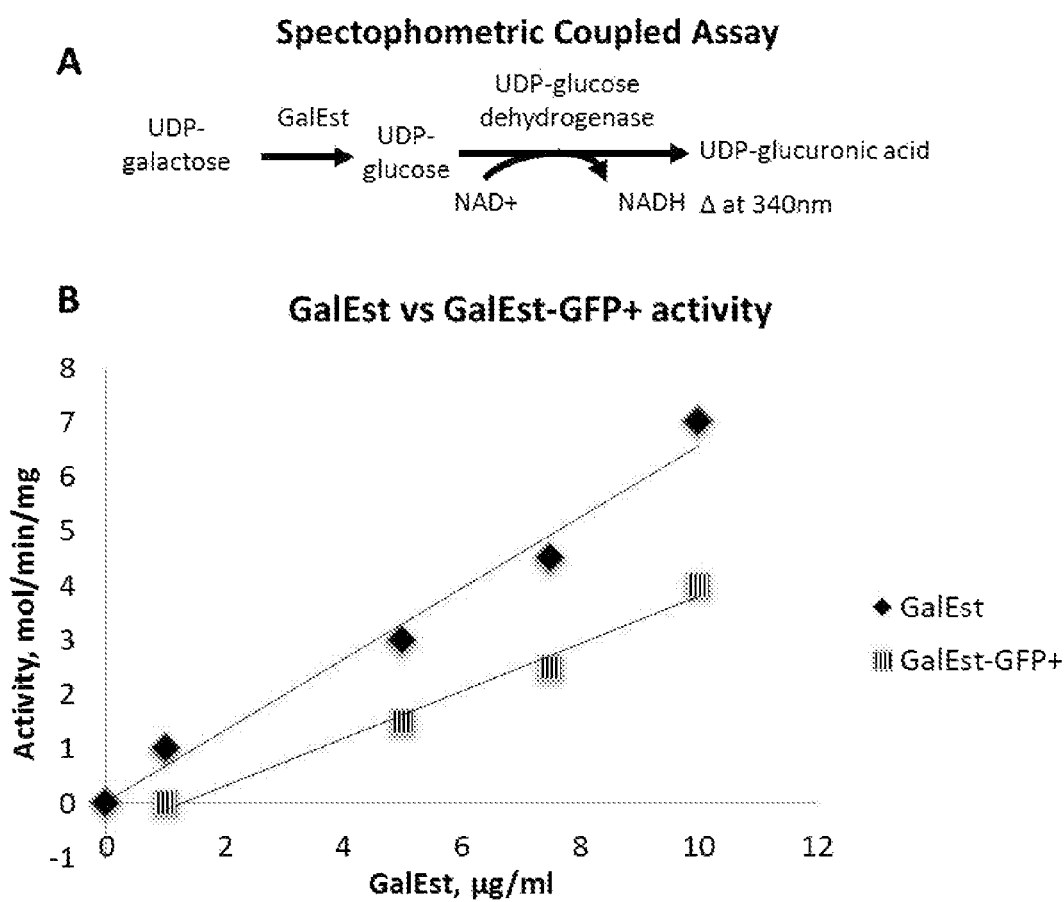

FIG. 7: Schematic of the spectrophotometric assay used for the detection of GalEst activity, as determined by NADH accumulation (measured at 340 nm) (A). Level of activity of different amounts of GalEst which are either free enzyme or linked to GFP+ via the isopeptide bond (B).

Figure 8:
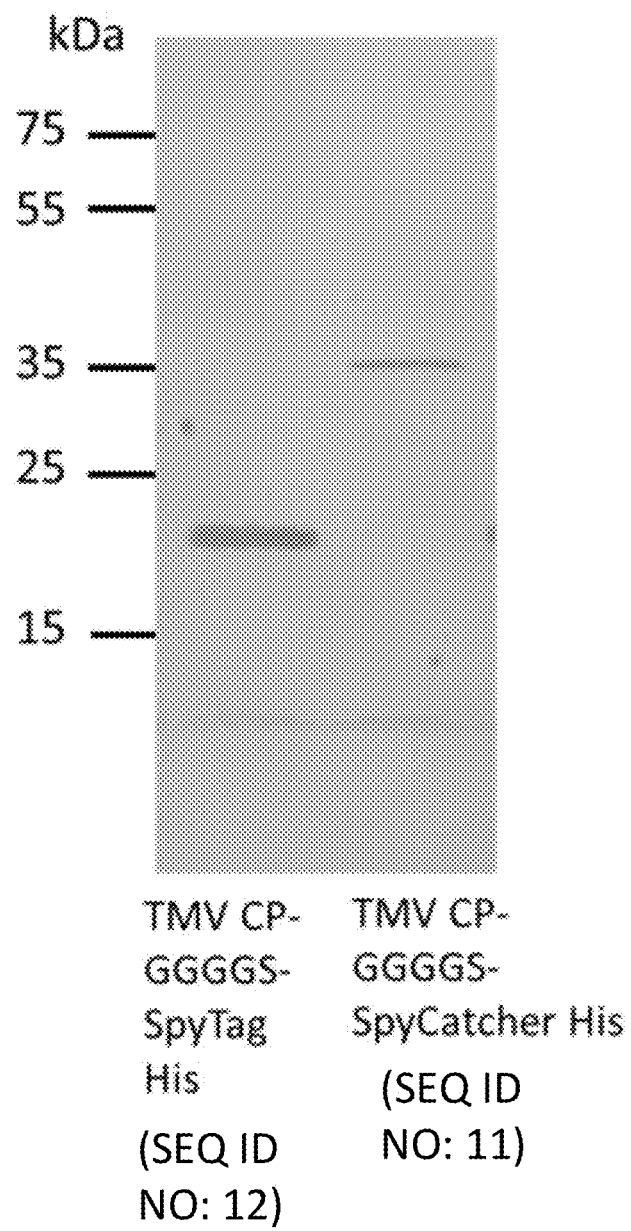

FIG. 8: Western blots of bacterially expressed TMV CP-GGGGS-SpyCatcher His (SEQ ID NO: 11) and TMV CP-GGGGS-SpyTag His (SEQ ID NO: 12), as detected by a specific 6× His antibody. Molecular weight markers are shown on the left-hand side.

Figure 9:
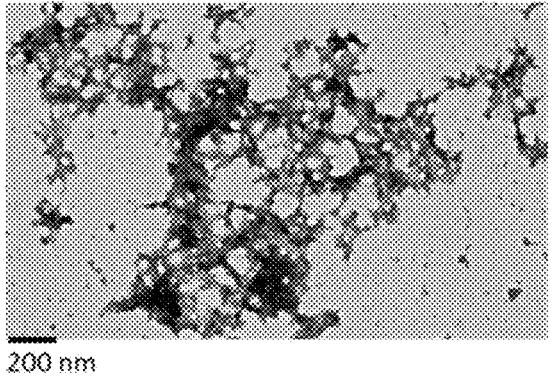
Figure 9:
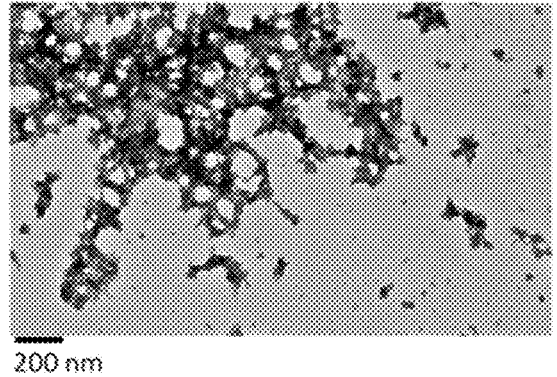

FIG. 9: Transmission electron microscopic imaging of TMV CP-GGGGS-SpyCatcher His (SEQ ID NO: 11) and TMV CP-GGGGS-SpyTag His (SEQ ID NO: 12) structures. Scale bars are shown.

Figure 10:
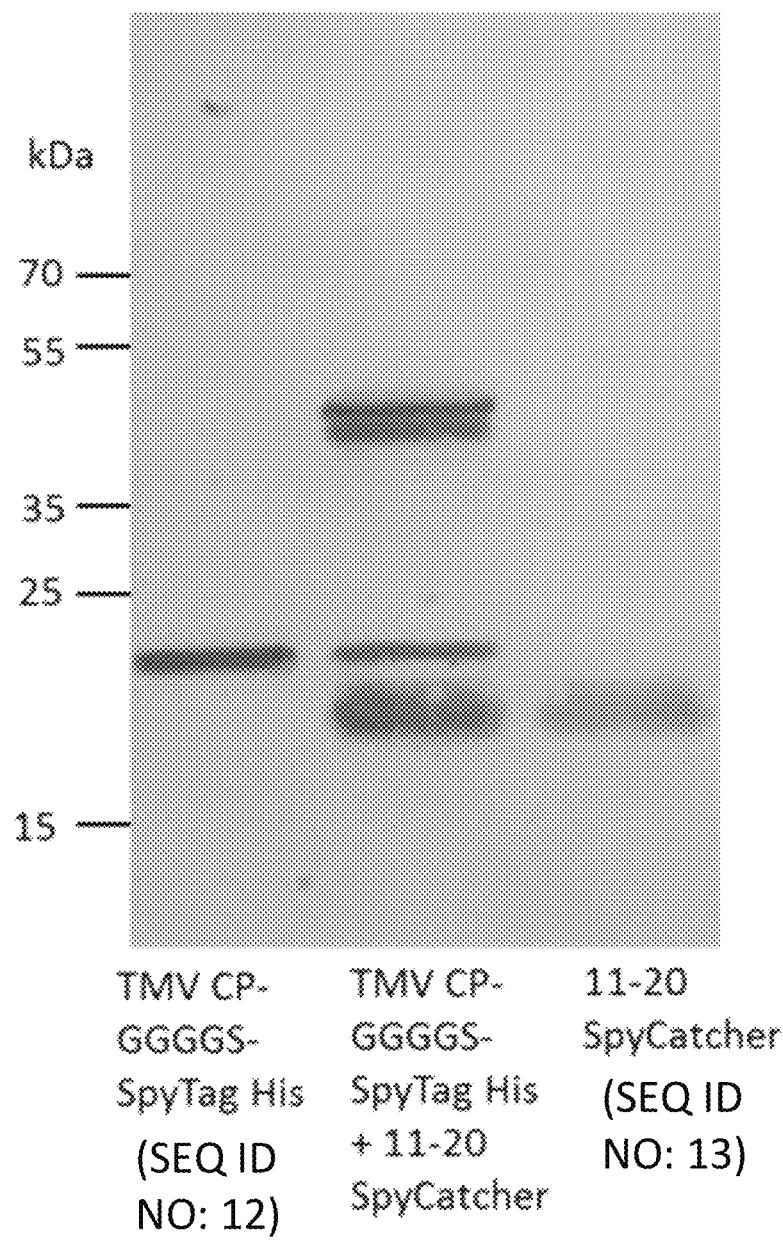

FIG. 10: Western blots of mixed and unmixed TMV CP-GGGGS-SpyTag His (SEQ ID NO: 12) and 11-20 SpyCatcher (SEQ ID NO: 13), as detected by a specific 6× His antibody. Molecular weight markers are shown on the left-hand side.

DETAILED DESCRIPTION

Bacteria which expressed either TMVc (TMV CP with the modified E50Q and D77N groups), TMVc* (TMVc into which a SpyTag was fused to the C-terminal end for surface display after assembly) or GFP+ (SpyCatcher fused to the N-terminus of GFP) were lysed and the lysates were mixed and then purified via a 20% sucrose cushion, prior to western blot analysis with GFP and TMV specific antibodies. Western blots probed with the TMV antibody (FIG. 1A) showed a strong specific band at the expected size of 17 kDa for the TMVc samples at the different purification stages, however a faint band ~18.5 kDa was observed for the TMVc*, a size increase which is consistent for TMVc with an inserted SpyTag (see bands denoted by #in FIG. 1A). The intensity of the TMVc* band may be less than TMVc since the SpyTag surface display may mask epitopes with which the TMV antibody may normally interact. GFP+ lysates only did not produce any bands after exposure to the TMV antibody, indicating specificity of the antibody (FIG. 1A).

In summary, TMVc and TMVc* are present in their respective lysates, during incubation and also after the sucrose cushion purification.

Prior to incubation of the lysates it was found that the GFP+ reacted strongly with the GFP antibody (FIG. 1 B), giving a band at the correct 45 kDa size and also a slightly smaller band which likely represents a cleavage product.

No reactivity was observed in the lysates derived from bacteria which expressed TMVc* or TMVc only, indicating specificity of the antibody. After incubation of the TMVc lysate with the GFP+, the GFP+ band size and pattern did not change relative to the GFP+ only control (FIG. 1 B). In contrast, with the TMVc* and GFP+ mixed and incubated lysates, the GFP+ bands had all become heavier by ~18 kDa. This is considered to indicate that the 18.5 kDa TMVc* could associate with the GFP+, and this linkage would likely be covalent in nature given that samples were prepared and boiled in denaturing conditions prior to loading onto SDS-PAGEs. After sucrose cushion purification (FIG. 1 B), GFP+ was lost from the GFP+ and TMVc/GFP+ lysates, whereas the large GFP+ band was recovered from the lysates of TMVc*/GFP+. This is considered to indicate that GFP+ covalently associates and co-purifies with TMVc* but not with TMVc. This is also supported by the UV illumination of pellets obtained after sucrose cushion purification, whereby GFP is strongly visible in TMVc*/GFP+ samples but not in TMVc/GFP+ or GFP+ only (FIG. 2). The heavy ~64 kDa TMVc*/GFP+ band observed in the GFP antibody probed western (FIG. 1 B, after incubation and also after sucrose cushion isolation) was not visible in the TMV antibody probed western (FIG. 1A). This is considered to indicate that the covalently linked GFP+ may further compromise TMV antibody accessibility to reactive epitopes on the TMVc* surface (inhibiting detection). In the TMV antibody probed western blot (FIG. 1A) faint ~18 kDa bands were observed in TMVc*/GFP+ lysates and this likely represents a population of TMVc* which had not reacted with the GFP+ and thus retained some affinity to the TMV antibody.

Expressed SpyTag-TMV coat proteins exist as networks and SpyCatcher-GFP forms spherical nanoparticles, which can interact to produce macroscale structures Samples of the TMVc*, TMVc and GFP+ after lysis, mixing and incubating and centrifugation were taken and assessed using transmission electron microscopy (TEM). Analysis of the TMVc bacterial lysates revealed rods which were 18 nm in diameter with a variable length which ranged from 40 nm to several microns (FIG. 3A, C).

In contrast, the TMVc* lysates contained network-like structures (FIG. 3 B), which on closer inspection were composed of shorter aggregated rods of precisely 18 nm diameter (FIG. 3 D).

The GFP+ lysates formed "spherical" particles which ranged in size from 50-100 nm in diameter (FIG. 3 E); structures which are in agreement with other reports in which GFP fusions were overexpressed in bacteria.

TMVc/GFP+ and TMVc*/GFP+ lysates were incubated and then purified using ultracentrifugation on sucrose cushions as described previously. The obtained structures were obtained using TEM with immunogold labelling with GFP antibodies. It was determined the GFP+ only particles were predominantly lost after ultracentrifugation on sucrose cushions (TEM image not shown) which is confirmatory to the data in FIGS. 1 and 2. Similarly with the TMVc/GFP+ there were very few GFP+ particles present, and when they were observed they did not obviously associate with the large numbers of TMVc rods which were successfully isolated from the sucrose cushions (FIG. 4A). In complete contrast, with the TMVc*/GFP+ sample, large numbers of GFP+ particles were present as aggregates (FIG. 4 B). This is considered to be representative of groups of GFP+ particles which have become covalently attached to TMVc* networks. To check that these aggregates were in fact GFP+, specific gold conjugated GFP antibodies which could decorate GFP+ particles (FIG. 4 C) were demonstrated to attach to the aggregated spherical structures (FIG. 4 D).

Structural associations were confirmed using immunotrapping TEM analysis. GFP+, TMVc or TMVc* were incubated separately with GFP antibody coated TEM grids. It was found that the GFP+ particles became immunotrapped (FIG. 5A), whereas neither TMVc nor TMVc* were retained on the grids (FIGS. 5 B and C respectively), which indicates specificity. TEM grids with the trapped GFP+ particles were incubated with either TMVc or TMVc* prior to treatment with TMV specific gold conjugated antibodies. This would permit binding of GFP+ by TMVc* to be confirmed. After incubation with the immunotrapped GFP+ grids (and subsequent washing steps), there were no obvious TMVc rods present and moreover there were extremely small numbers of gold labelled TMV antibodies present, which again indicated that there was no interaction between TMVc and GFP+ (FIG. 5 D). In GFP+ trapped grids incubated with the TMVc*, large aggregates which were heavily decorated with gold labelled TMV antibodies were found to be associated with GFP+ structures (FIG. 5 E). This suggests that the GFP+ can capture TMVc*. The TMV antibodies used were specific as indicated by their localization to purified bacterially produced TMVc rods (FIG. 5 F). In these experiments the TMVc* network structures were not so clearly discernible. This may be due to multiple layers of stacked network being deposited around the GFP+ particles, producing contrast differences which precluded observation of structural characteristics.

The TMV derived networks and GFP containing SpyCatcher or SpyTag can form covalent links with proteins containing the interacting partner, which may promote protein stability without abolishing protein activity.

To demonstrate the potential utility of the platforms, their capacity to interact with proteins of interest which were fused to either SpyTag or SpyCatcher were tested. In one such embodiment the interaction of GFP+ with a SpyTag fused to the N-terminal of Uridine 5'-diphosphogalactose 4-epimerase (GalEst), an economically important enzyme which can convert UDP-galactose into UDP-glucose, was tested. GalEst was expressed and purified from bacteria as discussed. In one embodiment nickel column isolated GFP+ was incubated with equimolar amounts of nickel column purified GalEst for different periods of time (5 minutes-16 hours). The formation of covalent bonds between the GalEst and GFP+ was assessed using denaturing coomassie stained SDS-PAGES. The isolated and unmixed GalEst and GFP+ samples gave distinct bands of the appropriate size (see FIG. 6). Mixing the GFP+ and GalEst and incubating them led to the formation of an upper band corresponding to GFP+ covalently linked to GalEst, which became more intense with longer incubation (FIG. 6); this was also accompanied by corresponding decreases in the unreacted GalEst and GFP+ bands. Interestingly when the GalEst was incubated separately for 16 hours prior to being combined with GFP+ and incubated for 10 minutes, many degradation products were observed (FIG. 6). This indicates that the GalEst is unstable and that the presence of the GFP+ soon after isolation greatly enhances GalEst stability. This indicates that the platform technology may act to stabilize proteins of interest via anchoring at one end.

In order to test that the GalEst-GFP+ complexes were still enzymatically active, these structures were tested in their capacity to convert UDP-galactose into UDP-glucose by using a coupled assay with which the level of conversion is stoichiometrically linked to changes in NADH, which can be detected by measuring absorbance at 340 nm (FIG. 7A). It was found that the GalEst-GFP+ complexes were still enzymatically active, but with a slight decrease in activities relative to the free unconjugated enzyme (FIG. 7 B). This indicates the platform can stabilize the enzyme without compromising its functionality.

In another embodiment we produced a variant of the TMVc* in which a linker sequence (3× repeat of GGGGS (residues 160 to 174 of SEQ ID NO: 11 or SEQ ID NO: 12)) is positioned between the C-terminal of the TMV CP and the SpyCatcher-6× his sequence (TMV CP-GGGGS-Spy-Catcher His (SEQ ID NO: 11)) or a SpyTag-6× his sequence (TMV CP-GGGGS-SpyTag His (SEQ ID NO: 12)). These constructs were designed to give the additional utility of potential nickel column isolation of the complexes and also to investigate whether inclusion of additional sequences can influence the expected formation of the network structures. The bacterially expressed constructs gave the correct size on western blots probed with a 6× His antibody (FIG. 8), whereby TMV CP-GGGGS-SpyCatcher His (SEQ ID NO: 11) was ~34 kDa and the TMV CP-GGGGS-SpyTag His (SEQ ID NO: 12) was ~21 kDa. Subsequent TEM analysis of the bacterially expressed and isolated structures indicated the formation of networks (FIG. 9), which were consistent with what was previously observed with the TMVc*. This suggests that addition of extra sequences into these constructs do not compromise network formation. To demonstrate that the constructs could still function to attach their interacting partners, the isolated TMV CP-GGGGS-SpyTag His (SEQ ID NO: 12) was mixed and incubated with a SpyCatcher fused to a potential vaccine antigen derived from the scab mite pathogen *Psoroptis ovis* (11-20 Spy-Catcher (SEQ ID NO: 13)). Subsequent western blot analysis using 6× His antibodies confirmed that the unmixed proteins were of the appropriate size and that when mixed, a band shift was detected indicating covalent association between the TMV CP-GGGGS-SpyTag His (SEQ ID NO: 12) and 11-20 SpyCatcher (SEQ ID NO: 13) (FIG. 10).

In summary, fusion of the SpyTag to the C-terminal of the E50Q and D77N modified TMV CP leads to formation of network like structures when expressed in bacteria. Moreover insertion of linker sequences (3× repeat of GGGGS (residues 160 to 174 of SEQ ID NO: 11 or SEQ ID NO: 12)), a 6× his tag and/or replacement of SpyTag with SpyCatcher in the TMV derived constructs does not compromise this network formation; indicating plasticity of the networks to support significant sequence alteration. In addition these can covalently bind GFP or an 11-20 sequence derived from a *P. ovis* antigen sequence fused to SpyCatcher, the interacting partner of the SpyTag. It is considered this can provide simplified production of large networks functionalized with proteins and/or enzymes, which do not involve crosslinker chemistries or multiple complex clean up steps. This work also indicates that GFP-Spycatcher spherical particles could have utility as a surface presentation platform.

Using methods as disclosed herein GFP particles of at least 500 nm in size can be provided. Fusing the SpyCatcher sequence to the N-terminal end of GFP without other modifications at the C-terminus led to production of smaller particles around 50-150 nm. Without wishing to be bound by theory, it is considered this size difference is likely a consequence of the shorter period of induction of expression in bacteria (typically less than 24 hours); however, the size difference may be influenced by the nature of the Spy-Catcher protein fused to the GFP. The GFP particles still reacted with the GFP antibody, indicating that the presence of the SpyCatcher does not completely mask the GFP surface. The SpyCatcher-GFP also interacted with the Spy-Tag on the surface of the TMV coat protein derived networks to form covalent interactions. It is considered the GFP-SpyCatcher particles produced could act as a fluorescent novel surface display system which may be decorated with any protein or enzyme which is fused to a SpyTag at its C-terminus; as was exemplified by the capacity of the GFP-SpyCatcher particles to bind and stabilize a uridine 5'-diphosphogalactose 4-epimerase, which retained its activity. Such interactions may also occur with proteins that have a SpyTag inserted into the central region or fused to the N-terminus. Although the GFP particles can act as a nanoscale surface display platform, it also has the advantage that it can covalently integrate into larger 3d structures (substrates/scaffolds). Suitably the integration of the GFP particles onto a larger 3d substrate/scaffold can be monitored by exploiting the fluorescence of the particles. Suitably the GFP particles may have multiple available SpyCatcher motifs which may not be fully utilized/occupied upon binding 3d macroscale scaffolds. These "free" Spycatcher sites can permit the further attachment of proteins of interest; effectively producing complexes with multifunctional decoration which may be controlled by GFP particles.

It is considered SpyTag can react with its interacting partner even under a wide range of temperatures (at least 4-37° C.), pH (at least 5-8), cation concentrations and non-ionic detergent conditions.

EXAMPLES

Example 1—Sequences and Plasmids

For the SpyTag-TMV (TMVc*), the TMV E50Q and D77N group modified coat protein sequence (TMVc; Brown et al., 2013) was fused at its C-terminal end to the SpyTag sequence (Long et al., 2013). For the SpyCatcher-GFP sequence (GFP+), SpyCatcher (Long et al., 2013) was fused to the N-terminal end of the eGFP sequence (GenBank: AAG27429.1). For the GalEst, this consisted of a UDP-glucose 4-epimerase sequence (GenBank: EIE36183.1) to which a 6 His and SpyTag sequence was attached at its N-terminal end. For the TMV CP-GGGGS SpyCatcher His (SEQ ID NO: 11), the TMVc* sequence had a 3×GGGGS linker-6 His-SpyCatcher fused to its C-terminal end. For the TMV CP-GGGGS-SpyTag His (SEQ ID NO: 12), a 3×GGGGS linker-SpyTag-6 His, was fused to the C-terminal end of the TMVc*. For the 11-20 SpyCatcher (SEQ ID NO: 13), a small *Psoroptes ovis* peptidic sequence was fused to the C-terminal of the SpyCatcher. These were codon optimized for bacterial expression and cloned into a pET-21a(+) vector by Genscript (Piscataway, USA). The TMV-VLP (TMVc) control (with no tags) was produced in a similar manner. Plasmids were transformed into BL21(DES) pLysS (ThermoFisher Scientific, Paisley, UK) or Lemo 21 (New England Biolabs, Hitchin, UK) competent cells by following the manufacturers recommendations.

Example 2—Expression in Bacteria and Isolation of Proteins or Virus Structures

Bacteria containing the plasmids were grown at 37° C. with shaking at 200 rpm in LB media supplemented with 100 μg/ml ampicillin and 34 μg/ml chloramphenicol. Once cultures reached an OD 600 of 0.5, IPTG was added to a final concentration of 0.1 mM, and induction proceeded overnight at 20° C. with shaking at 200 rpm. Bacteria were pelleted by centrifugation at 4000 g for 15 minutes, the supernatant was removed and the cells were lysed by freeze-thawing 3 times using liquid nitrogen and a 37° C. water bath, before proceeding with protein extraction using the B-PER Complete reagent (ThermoFisher Scientific, Paisley, UK). Lysates obtained with the B-PER Complete reagent were centrifuged at 10,000 g for 20 minutes to remove debris. The lysates were combined (TMVc* or TMVc were mixed with GFP+) in equal volume and incubated at room temperature for 1 hour prior to centrifugation on a 20% sucrose cushion, after which the pellet was resuspended in water for western blot analysis. Alternatively, the lysates were kept separate and more rigorously purified for future electron microscope analysis.

For isolation of TMV CP-GGGGS-SpyCatcher His (SEQ ID NO: 11), TMV CP-GGGGS-SpyTag His (SEQ ID NO: 12), and 11-20 SpyCatcher (SEQ ID NO: 13), B-PER complete cell lysates were obtained and further purification was carried out using standard nickel columns according to manufacturers protocols (Qiagen, Manchester, UK). The TMV CP-GGGGS-SpyCatcher His (SEQ ID NO: 11) and TMV CP-GGGGS-SpyTag His (SEQ ID NO: 12) were subsequently analyzed using TEM as described below, or were mixed with 11-20 SpyCatcher (SEQ ID NO: 13) and observed on His antibody probed western blots.

Material for the enzymatic assays (GalEst and GFP+) was isolated from bacterial lysates using generic nickel column and anion exchange purification procedures.

Example 3—TMVc* and TMVc Purification and Buffer Exchange of GFP+ Prior to Transmission Electron Microscopy To the centrifuged TMV structure lysates, PEG 8000 and NaCl were added to a final concentration of 2% and 1% respectively, and the solutions were incubated at 4° C. overnight to ensure precipitation. These were centrifuged at 10000 g at 4° C. for 20 minutes to pellet the virus structures. The pellets were resuspended in 25 mM tris-HCl (pH 7.8), centrifuged at 10000 g to clarify and the supernatants were collected. Another two rounds of resuspension and centrifugation was carried out to obtain maximal virus structure yields, while minimizing debris. The clarified supernatants were then loaded onto 2 ml 20% sucrose 25 mM Tris-HCl (pH 7.8) cushions, which was then centrifuged in swing out rotors (SW41 Beckman Coulter; Beckman Coulter, California, USA) at 32000 rpm for 2 hours at 4° C. Pellets were resuspended in 0.01 M Tris-HCl (pH 7.8), ultracentrifuged at 32000 rpm for 2 hours at 4° C. in a SW41 rotor, with the pellet resuspended in water. Virus structures were retained for future electron microscopic analysis.

Example 4—Transmission Electron Microscopy (TEM) and TEM Immunotrappinq

TMVc*, TMVc, GFP+, TMVc/GFP or TMVc*/GFP, or TMV CP-GGGGS-SpyCatcher His (SEQ ID NO: 11) and TMV CP-GGGGS-SpyTag His (SEQ ID NO: 12), were diluted in sterile filtered distilled water, and 30 µl was placed onto carbon-coated copper grids for 1 minute, wicked off and stained with 2% uranyl acetate, washed twice with 20 µl water, dried and examined in a JEOL 1400 transmission electron microscope (TEM) at 80 kV, or were used for GFP antibody work where appropriate. For detection of GFP+ in the prepared GFP+, TMVc/GFP+ or TMVc*/GFP+ grids, 50 µl of blocking buffer (1% BSA, 0.05% TWEEN, 1×PBS) was applied for 0.5 hours prior to a 1 hour room temperature incubation with a rabbit GFP antibody (Abcam, Cambridge, UK; ab6556) diluted 1/50 in blocking buffer. This was followed by three 50 µl washes in washing buffer (0.25% BSA, 0.05% TWEEN, 1×PBS) before incubation for 1 hour with 50 µl of a goat anti-rabbit 5 nm gold conjugated antibody (ab27235; abcam, Cambridge, UK) diluted 1/50 in blocking buffer. Grids were then washed by rinsing with 50 µl washing buffer 3 times, followed by a single 50 µl wash in water prior to drying and then observation under TEM.

For immunotrapping experiments, mouse GFP antibodies (ab1218; abcam, Cambridge, UK) were diluted 1/1000 in 1×PBS and 30 µl was applied to carbon coated grids and incubated for 1.5 hours at 37° C. These grids were subsequently washed twice in 1×PBS by incubating them each time for 10 minutes on a rotating table. Grids were then floated on GFP+ (in 1×PBS) or purified TMVc or TMVc* for 2 hours at room temperature prior to washing in 1×PBS, staining in 2% uranyl acetate, washed twice in water and viewing under EM.

Grids onto which GFP+ had been immunotrapped (prepared as above but not uranyl acetate treated), were floated on dilutions of TMVc or TMVc* for 1.5 hours in 1×PBS at room temperature. After washing in washing buffer (on a rotating table as before), the grids were floated on TMV rabbit antisera which was diluted 1/200 in blocking buffer and incubated for 1 hour at room temperature. This was followed by washing in washing buffer, and then a 1 hour incubation with a goat anti-rabbit 5 nm gold conjugated antibody diluted 1/50 in blocking buffer. Grids were then washed by rinsing with 50 µl washing buffer 3 times, followed by a single 50 µl wash in water prior to drying and then observation under TEM.

Example 5—GalEst and GalEst-GFP+ Enzyme Assays

The following reagents were combined per 1 ml reaction: 0.125 M Bicinate pH 8.5, 1.25 mM NAD+, 2 µg UDP-glucose dehydrogenase (UGDH-729H: Creative Biomart, USA), 1-10 µg GalEst or GalEst-GFP+. These were equilibrated for 5 minutes at 27° C. prior to addition of 0.8 mM UDP-galactose substrate. The reaction kinetics were determined over a 10 minute period by measuring the A prior.

Example 6—SDS PAGEs and Western Blot Detection

Protein samples were mixed 1:4 parts with 4× Laemmli loading buffer and then boiled for 10 minutes to denature the proteins. Twenty microliters of each of these samples were loaded onto 15% SDS-PAGE gels, along with 15 µl of PageRuler Plus prestained ladder (ThermoFisher Scientific, Paisley, UK). Gels were either coomassie stained using established methods or were electroblotted onto Immobilon-P membrane (Millipore, Watford, UK) by following the manufacturer's recommendations. The Immobilon-P membrane was blocked by incubating in 1×PBS, 1% BSA and 0.05% TWEEN, for 1 hour. Anti-TMV or anti-GFP (abcam, Cambridge, UK; ab6556) antibodies raised in rabbits, or anti-his antibodies raised in mouse (H1029—0.2 ml; Sigma Dorset) were added to the membranes in blocking solution at either 1/10000 or 1/5000 dilutions and incubated with shaking at room temperature for 1 h. After washing, an anti-rabbit IgG alkaline phosphatase conjugate (A8025—1 ML; Sigma, Dorset, UK) or anti-mouse IgG alkaline phosphatase conjugate (A9316—0.25 ml) was added to the blots at a concentration of 1/1000 in blocking buffer. After incubation at room temperature under shaking conditions the blots were washed and covered with BCIP/NBT (B1911; Sigma, Dorset, UK). The blots were left to develop for 10 min, after which banding was visible. The developed blots were scanned and saved as jpeg images.

Although the invention has been particularly shown and described with reference to particular examples, it will be understood by those skilled in the art that various changes in the form and details may be made therein without departing from the scope of the present invention.

REFERENCES

Marsian, J., Lomonossoff, G. P., Molecular pharming-VLPs made in plants. *Curr. Op. Biotech.* 2016, 37, 201-206.

Koch, C., Eber, F. J., Azucena, C., Forste, A. et al., Novel roles for well-known players: from tobacco mosaic virus pests to enzymatically active assemblies. *Beilstein J. Nanotech.* 2016, 7. DOI: 10.3762/bjnano.7.54.

Thuenemann, E. C., Lenzi, P., Love, A. J. et al., The Use of Transient Expression Systems for the Rapid Production of Virus-like Particles in Plants. *Curr. Pharm. Des.* 2013, 19, 5564-5573.

Love, A. J., Makarov, V., Yaminsky, I., Kalinina, N. O. et al., The use of tobacco mosaic virus and cowpea mosaic virus for the production of novel metal nanomaterials. *Virology*, 2014, 449, 133-139.

Cuenca, S., Mansilla, C., Aguado, M., Yuste-Calvo, C., Sanchez, F., Sanchez-Montero, J. M., Ponz, F., Nanonets derived from the Turnip mosaic virus as scaffolds for increased enzymatic activity of immobilized *Candida Antarctica* Lipase B. *Front. Plant Sci.* 2016, 7, 464.

Chatterji, A., Ochoa, W., Shamieh, L., Salakian, S. P., Wong, S. M. et al., Chemical conjugation of heterologous proteins on the surface of Cowpea mosaic virus. *Bioconjug. Chem.* 2004, 15, 807-813.

Aljabali, A. A., Barclay, J. E., Steinmetz, N. F., Lomonossoff, G. P., Evans, D. J., Controlled immobilization of active enzymes on the cowpea mosaic virus capsid. *Nanoscale*, 2013, 5640-5645.

Stubbs, G., Molecular structures of viruses from the tobacco mosaic virus group. *Semin. Virol.* 1990, 1, 405-412.

Brown, A. D., Naves, L., Wang, X., Ghodssi, R., Culver, J. N., Carboxylate-directed in vivo assembly of virus-like nanorods and tubes for the display of functional peptides and residues. *Biomacromol.* 2013, 14, 3123-3129.

Bendahmane, M., Chen, I., Asurmendi, S., Bazzini, A. A., Szecsi, J., Beachy, R. N., Coat protein-mediated resistance to TMV infection of *Nicotiana tabacum* involves multiple modes of interference by coat protein. *Virology*, 2007, 366, 107-116.

Bruckman, A. M., Steinmetz, N. F., Chemical modification of the inner and outer surfaces of tobacco mosaic virus (TMV). *Methods Mol. Biol.* 2014, 1108, 173-185.

Aljabali, A. A. A., Barclay, J. E., Butt, N. J., Lomonossoff, G. P., Evans, D. J., Redox-active ferrocene-modified Cowpea mosaic virus nanoparticles. *Dalton Trans.* 2010, 39, 7569-7574.

Tinazzi, E., Merlin, M., Bason, C., Beri, R., Zampieri, R., et al., Plant-dereived chimeric virus particles for he diagnosis of primary Sjogren syndrome. *Front. Plant. Sci.* 2015, 6, 1080.

Besong-Ndika, J., Wahlsten, M., Cardinale, D., Pille, J., Walter, J., et al., Toward the reconstitution of a two enzyme cascade for resveratrol synthesis on potvirus particles. *Front. Plant. Sci.* 2016, 7, 89.

Zackeri, B., Fierer, J. O., Celik, E., Chittock, E. C. et al., Peptide tag forming a rapid covalent bond to a protein, through engineering a bacterial adhesion. *Proc. Nat. Acad. Sci. USA.* 2012, 109, 690-697.

Long, L., Fierer, J. O., Rapoport, T. A., Howarth, M., Structural analysis and optimization of the covalent association between SpyCatcher and a peptide tag. *J. Mol. Biol.* 2014, 426, 309-317.

Thrane, S., Janitzek, C. M., Matondo, S., Resende, M. et al., Bacterial superglue enables easy development of efficient virus-like particle based vaccines. *J. Nanobiotech.* 2016, 14, 30.

Brune, K. D., Leneghan, D. B., Brian, I. J., Ishizuka, A. S., Plug and display: decoration of virus-like particles via isopeptide bonds for modular immunization. *Sci. Reports*, 2016, 6, 19234.

Reddington, S. C., Howarth, M., Secrets of a covalent interaction for biomaterials and biotechnology: SpyTag and SpyCatcher. *Curr. Op. Chem. Biol.* 2015, 29, 94-99.

Zakeri, B., Fierer, J. O., Celik, E., Chittock, E. C., Schwarz-Linek, U., Moy, V. T., Howarth, M., Peptide tag forming a rapid covalent bond to a protein, through engineering a bacterial adhesion. *Proc. Natl. Acad. Sci.* 2012, 109, 690-697.

Venning-Slater, M., Hooks, D. O., Rehm, H. A., In vivo self-assembly of stable green fluorescent protein fusion particles and their uses in enzyme immobilization. *App. Environ. Micro.* 2014, 80, 10.

Jahns, A. C., Maspolim, Y., Chen, S., Guthrie, J. M., Blackwell. L. F., Rehm, B. H. A., In vivo self assembly of fluorescent protein microparticles displaying specific binding domains. *Bioconj. Chem.* 2013, 24, 1314-1323.

Love A., Makarov V., Sinitsyna O., Shaw J., Yaminsky I., Kalinina N., Taliansky M., A genetically modified tobacco mosaic virus that can produce gold nanoparticles from a metal salt precursor. Frontiers in Plant Science, 2015, 6, 984

```
SpyCatcher sequence (AFD50637.1)
                                          (SEQ ID NO: 1)
MSYYHHHHHHDYDIPTTENLYFQGAMVDTLSGLSSEQGQSGDMTIEEDSAT

HIKFSKRDEDGKELAGATMELRDSSGKTISTWISDGQVKDFYLYPGKYTFV

ETAAPDGYEVATAITFTVNEQGQVTVNGKATKGDAHI
6 His highlighted in Bold
TEV cleavage sequence underlined SpyTag
                                          (SEQ ID NO: 2)
AHIVMVDAYKPTK SpyTag truncated
                                          (SEQ ID NO: 3)
AHIVMVDA TMV CP (modified for self assembly in bacteria)
                                          (SEQ ID NO: 4)
MSYSITTPSQFVFLSSAWADPIELINLCTNALGNQFQTQQARTVVQRQFSQ

VWKPSPQVTVRFPDSDFKVYRYNAVLNPLVTALLGAFDTRNRIIEVENQAN

PTTAETLDATRRVDDATVAIRSAINNLIVELIRGTGSYNRSSFESSSGLVW
```

TSGPAT
Modification site to introduce PmlI indicated in bold and underlined

TMV CP with C-terminal SpyTag
(SEQ ID NO: 5)
MSYSITTPSQFVFLSSAWADPIELINLCTNALGNQFQTQQARTVVQRQFSQ
VWKPSPQVTVRFPDSDFKVYRYNAVLNPLVTALLGAFDTRNRIIEVENQAN
PTTAETLDATRRVDDATVAIRSAINNLIVELIRGTGSYNRSSFESSSGLVW
TSGPATAHIVMVDAYKPTK
Modification site to introduce PmlI indicated in bold and underlined GFP sequence (ADQ48006.1)
(SEQ ID NO: 6)
MVSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFFK
DDGNYKTRAEVKFEGDTLVNRIELKGIDFKEDGNILGHKLEYNYNSHNVYI
MADKQKNGIKVNFKIRHNIEDGSVQLADHYQQNTPIGDGPVLLPDNHYLST
QSALSKDPNEKRDHMVLLEFVTAAGITLGMDELYKSGLRSRAQASNSAVDG
TAGPGSTGSR SpyCatcher-GFP
(SEQ ID NO: 7)
MSYYHHHHHHDYDIPTTENLYFQGAMVDTLSGLSSEQGQSGDMTIEEDSAT
HIKFSKRDEDGKELAGATMELRDSSGKTISTWISDGQVKDFYLYPGKYTFV
ETAAPDGYEVATAITFTVNEQGQVTVNGKATKGDAHIATCMVSKGEELFTG
VVPILVELDGDVNGHKFSVSGEGEGDATYGKLTLKFICTTGKLPVPWPTLV
TTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKV
NFKIRHNIEDGSVQLADHYQQNTPIGDGPVLLPDNHYLSTQSALSKDPNEK
RDHMVLLEFVTAAGITLGMDELYKSGLRSRAQASNSAVDGTAGPGSTGSR
Linker sequence shown in bold and underlined NCBI Entrez Code AAK33238
(SEQ ID NO: 8)
MKLRHLLLTGAALTSFAATTVHGETVVNGAKLTVTKNLDLVNSNALIPNTD
FTFKIEPDTTVNEDGNKFKGVALNTPMTKVTYTNSDKGGSNTKTAEFDFSE
VTFEKPGVYYYKVTEEKIDKVPGVSYDTTSYTVQVHVLWNEEQQKPVATYI
VGYKEGSKVPIQFKNSLDSTTLTVKKKVSGTGGDRSKDFNFGLTLKANQYY
KASEKVMIEKTTKGGQAPVQTEASIDQLYHFTLKDGESIKVTNLPVGVDYV
VTEDDYKSEKYTTNVEVSPQDGAVKNIAGNSTEQETSTDKDMTITFTNKKD
FEVPTGVAMTVAPYIALGIVAVGGALYFVKKNA NCBI Entrez Accession code NP_814829
(SEQ ID NO: 9)
MTKSVKFLVLLLVMILPIAGALLIGPISFGAELSKSSIVDKVELDHTTLYQ
GEMTSIKVSFSDKENQKIKPGDTITLTLPDALVGMTENDSSPRKINLNGLG
EVFIYKDHVVATFNEKVESLHNVNGHFSFGIKTLITNSSQPNVIETDFGTA
TATQRLTIEGVTNTETGQIERDYPFFYKVGDLAGESNQVRWFLNVNLNKSD
VTEDISIADRQGSGQQLNKESFTFDIVNDKETKYISLAEFEQQGYGKIDFV
TDNDFNLRFYRDKARFTSFIVRYTSTITEAGQHQATFENSYDINYQLNNQD
ATNEKNTSQVKNVFVEGEASGNQNVEMPTEESLDIPLETIDEWEPKTPTSE
QATETSEKTDTTETAESSQPEVHVSPTEEENPDEGETLGTIEPIIPEKPSV
TTEENGTTETAESSQPEVHVSPTEEENPDESETLGTIEPIIPEKPSVTTEE
NGTTETAESSQPEVHVSPAEEENPDESETLGTILPILPEKPSVTTEENGTT
ETAESSQPEVHVSPTEEENPDESETLGTIAPIIPEKPSVTTEENGITETAE
SSQPEVHVSPTKEITTTEKKQPSTETTVEKNKNVTSKNQPQILNAPLNTLK
NEGSPQLAPQLLSEPIQKLNEANGQRELPKTGTTKTPFMLIAGILASTFAV
LGVSYLQIRKN GalEst
(SEQ ID NO: 10)
MHHHHHHAHIVMVDAYKPTK
*MRVLVTGGSGYIGSHTCVQLLQNGHDVIILDNLCNSKRSVLPVIERLGGKH*
*PTFVEGDIRNEALMTEILHDHAIDTVIHFAGLKAVGESVQKPLEYYDNNVN*
*GTLRLISAMRAANVKNFIFSSSATVYGDQPKIPYVESFPTGTPQSPYGKSK*
*LMVEQILTDLQKAQPDWSIALLRYFNPVGAHPSGDMGEDPQGIPNNLMPYI*
*AQVAVGRRDSLAIFGNDYPTEDGTGVRDYIHVMDLADGHVVAMEKLANKPG*
*VHIYNLGAGVGNSVLDVVNAFSKACGKPVNYHFAPRREGDLPAYWADASKA*
*DRELNWRVTRTLDEMAQDTWHWQSRHPQGYPD*
6 His and SpyTag sequence shown in bold and underlined. Italicized sequence corresponds to GenBank: EIE36183.1.

TMV CP-GGGGS-SpyCatcher His
(SEQ ID NO: 11)
MSYSITTPSQFVFLSSAWADPIELINLCTNALGNQFQTQQARTVVQRQFSQ
VWKPSPQVTVRFPDSDFKVYRYNAVLNPLVTALLGAFDTRNRIIEVENQAN
PTTAETLDATRRVDDATVAIRSAINNLIVELIRGTGSYNRSSFESSSGLVW
TSGPATGGGGSGGGGSGGGGSMSYYHHHHHHDYDIPTTENLYFQGAMVDTL
SGLSSEQGQSGDMTIEEDSATHIKFSKRDEDGKELAGATMELRDSSGKTIS
TWISDGQVKDFYLYPGKYTFVETAAPDGYEVATAITFTVNEQGQVTVNGKA
TKGDAHI
3x GGGGS linker and 6 His sequences shown in bold and underlined TMV CP-GGGGS-SpyTag His
(SEQ ID NO: 12)
MSYSITTPSQFVFLSSAWADPIELINLCTNALGNQFQTQQARTVVQRQFSQ
VWKPSPQVTVRFPDSDFKVYRYNAVLNPLVTALLGAFDTRNRIIEVENQAN
PTTAETLDATRRVDDATVAIRSAINNLIVELIRGTGSYNRSSFESSSGLVW
TSGPATGGGGSGGGGSGGGGSAHIVMVDAYKPTKHHHHHH
3x GGGGS linker and 6 His sequences shown in bold and underlined 11-20 SpyCatcher
(SEQ ID NO: 13)
MSYYHHHHHHDYDIPTTENLYFQGAMVDTLSGLSSEQGQSGDMTIEEDSAT
HIKFSKRDEDGKELAGATMELRDSSGKTISTWISDGQVKDFYLYPGKYTFV
ETAAPDGYEVATAITFTVNEQGQVTVNGKATKGDAHILDIVADINGVQIEV
PILPTTKAKIIAKIIG
The *P. ovis* peptidic sequence is shown in bold and underlined.

The invention claimed is:

1. A macromolecular complex comprising a first and second complex
   wherein
   a) the first complex comprises a virus derived self-assembled micron scale macromolecular network structure comprising a tobacco mosaic virus (TMV) coat protein which surface displays a motif for one of a peptide tag and binding protein pair that can spontaneously form covalent linkages with the second complex wherein the peptide tag and binding protein pair are SpyTag and SpyCatcher, and b) the second complex comprises a particle which surface displays a motif interacting partner encoding one of the corresponding peptide tag and binding protein pair, wherein the first complex is covalently linked to the second complex.

2. The macromolecular complex of claim 1 wherein the first complex comprising a virus derived self-assembled micron scale structure is formed from virus protein aggregates or Virus Like Particles (VLP).

3. The macromolecular complex of claim 1 wherein the first complex of a virus derived micron scale structure comprises SpyTag and the second complex comprises green fluorescent particle (GFP) comprising SpyCatcher wherein the first complex is covalently linked to the second complex.

4. The macromolecular complex of claim 1 wherein the second complex comprising GFP and SpyCatcher is at least around 50-100 nanometers in size.

5. The macromolecular complex of claim 1 comprising a SpyTag decorated virus derived self-assembled micron scale structure covalently linked to a second complex comprising GFP comprising SpyCatcher wherein the SpyTag is provided to the N-terminus of a virus of the virus derived self-assembled micron scale structure.

6. The macromolecular complex of claim 1 comprising a first complex comprising a SpyTag decorated virus derived self-assembled micron scale structure covalently linked to a second complex comprising GFP comprising SpyCatcher wherein the SpyTag is provided at the C-terminus of a virus of the virus derived self-assembled micron scale structure.

7. The macromolecular complex of claim 1 comprising a first complex comprising a SpyTag decorated virus derived self-assembled micron scale structure covalently linked to a second complex comprising GFP comprising SpyCatcher wherein the SpyTag is provided between the N and C-terminus of a virus of the virus derived self-assembled micron scale structure.

8. The macromolecular complex of claim 1 wherein the TMV coat protein includes a modified coat protein E50Q and D77N, potato virus Y, potato virus X, tobacco rattle virus, or bacteriophage coat proteins.

9. The macromolecular complex of claim 1 wherein the virus derived self-assembled micron scale structure comprises a SpyTag at the C-terminal end of a TMV coat protein.

10. A nanoscale surface display system which binds to a first complex comprising a virus derived self-assembled micron scale macromolecular network structure comprising a tobacco mosaic virus (TMV) coat protein, wherein the virus derived self-assembled micron scale structure comprises a first member of a covalently reactive peptide tag and binding protein pair, wherein the peptide tag and binding protein pair are SpyTag and SpyCatcher, wherein the peptide tag and binding protein pair are capable of spontaneously forming a covalent bond, the nanoscale display surface comprising a second member of a covalently reactive peptide tag and binding protein pair that spontaneously forms a covalent bond with the first member.

11. The nanoscale surface display system of claim 10 which binds to a first complex comprising SpyTag the nanoscale surface display system comprising green fluorescent protein and further comprising SpyCatcher.

12. The nanoscale surface display system of claim 10 which binds to a first complex comprising SpyCatcher the nanoscale surface display system comprising green fluorescent protein and further comprising SpyTag.

13. A virus derived self-assembled micron scale macromolecular network structure comprising a tobacco mosaic virus (TMV) coat protein, wherein the micron scale macromolecular network structure is capable of binding to a second complex comprising a nanoscale display surface, the nanoscale display surface comprising a second member of a covalently reactive peptide tag and binding protein pair, wherein the peptide tag and binding protein pair are SpyTag and SpyCatcher, wherein the micron scale structure comprises a first member of a covalently reactive peptide tag and binding protein pair wherein the peptide tag and binding protein pair are capable of spontaneously forming a covalent bond.

14. The virus derived self-assembled micron scale structure capable of binding to a nanoscale surface display surface of claim 13 wherein the micron scale structure comprises self-assembled tobacco mosaic virus (TMV) coat protein comprising SpyTag.

15. The virus derived self-assembled micron scale structure capable of binding to a nanoscale surface display surface of claim 13 wherein the TMV includes a modified coat protein E50Q and D77N, potato virus Y, potato virus X, tobacco rattle virus, or bacteriophage coat proteins.

16. The virus derived self-assembled micron scale structure capable of binding to a nanoscale surface display surface of claim 13, wherein the TMV-derived structure comprises a SpyTag at the C-terminal end of the TMV coat protein.

17. The macromolecular complex of claim 1, wherein the second complex comprises a spherical green fluorescent particle (GFP) comprising SpyCatcher at its C-terminal end.

* * * * *